US009138711B2

(12) United States Patent
Treadway et al.

(10) Patent No.: US 9,138,711 B2
(45) Date of Patent: Sep. 22, 2015

(54) STABLE NANOPARTICLES AND METHODS OF MAKING AND USING SUCH PARTICLES

(75) Inventors: Joseph Treadway, Eugene, OR (US); Eric Tulsky, Berkeley, CA (US); Eric Welch, Eugene, OR (US)

(73) Assignee: Life Technologies Corporation, Carlsbad, CA (US)

( * ) Notice: Subject to any disclaimer, the term of this patent is extended or adjusted under 35 U.S.C. 154(b) by 1122 days.

(21) Appl. No.: 13/125,562

(22) PCT Filed: Oct. 23, 2009

(86) PCT No.: PCT/US2009/061953
§ 371 (c)(1),
(2), (4) Date: Jun. 1, 2011

(87) PCT Pub. No.: WO2010/048581
PCT Pub. Date: Apr. 29, 2010

(65) Prior Publication Data
US 2011/0226991 A1    Sep. 22, 2011

Related U.S. Application Data

(60) Provisional application No. 61/108,425, filed on Oct. 24, 2008, provisional application No. 61/144,613, filed on Jan. 14, 2009.

(51) Int. Cl.
*B01J 13/22*       (2006.01)
*C09K 11/02*     (2006.01)
(Continued)

(52) U.S. Cl.
CPC .................. *B01J 13/22* (2013.01); *B82Y 30/00* (2013.01); *B82Y 40/00* (2013.01); *C09K 11/02* (2013.01); *C09K 11/08* (2013.01); *C09K 11/025* (2013.01)

(58) Field of Classification Search
CPC .... C09K 11/06; C09K 11/025; C09K 11/565; C09K 11/883; C09K 11/584; C09K 11/642; C09K 11/70; H05B 33/14; H05B 33/10; H05B 33/145; H01L 33/502; H01L 33/504; H01L 51/5012; C12Q 1/6869; C12N 9/1252
USPC ....... 252/301.4 R, 301.4 H, 301.4 S, 301.6 S, 252/301.16, 301.36, 301.6 R, 301.4 P; 313/501–507, 499; 428/402, 690; 435/6.1, 188
See application file for complete search history.

(56) References Cited

U.S. PATENT DOCUMENTS 5,262,357 A    11/1993    Alivisatos et al.
5,505,928 A     4/1996    Alivisatos et al.
(Continued)

FOREIGN PATENT DOCUMENTS

CN    101040183 A    9/2007
CN    101194372 A    6/2008
(Continued)

OTHER PUBLICATIONS http://www.merriam-webster.com/dictionary/monolayer, printed Sep. 4, 2014.*
(Continued)

*Primary Examiner* — Matthew E Hoban
*Assistant Examiner* — Lynne Edmondson
(74) *Attorney, Agent, or Firm* — Life Technologies Corporation

(57) ABSTRACT

A population of nanoparticles is disclosed. The population is comprised of a plurality of core/shell nanocrystals, each including: a semiconductor core, an intermediate semiconductor shell layer disposed over the semiconductor core, an external semiconductor shell layer disposed over the intermediate semiconductor shell layer, and a hydrophilic organic layer in direct contact with the external semi-conductor shell layer. The population of nanoparticles has a $\alpha_{on}$ value of less than about 1.4.

28 Claims, 6 Drawing Sheets

(51) Int. Cl.
C09K 11/08 (2006.01)
B82Y 30/00 (2011.01)
B82Y 40/00 (2011.01)

(56) References Cited

U.S. PATENT DOCUMENTS

| | | | |
|---|---|---|---|
| 5,690,807 A | 11/1997 | Clark, Jr. et al. | |
| 5,990,479 A | 11/1999 | Weiss et al. | |
| 6,048,616 A | 4/2000 | Gallagher et al. | |
| 6,207,299 B1 | 3/2001 | Krauth | |
| 6,251,303 B1* | 6/2001 | Bawendi et al. | 252/301.4 R |
| 6,306,610 B1 | 10/2001 | Bawendi et al. | |
| 6,322,901 B1 | 11/2001 | Bawendi et al. | |
| 6,815,064 B2 | 11/2004 | Treadway et al. | |
| 7,172,791 B2 | 2/2007 | Treadway et al. | |
| 8,637,082 B2* | 1/2014 | Tulsky et al. | 424/489 |
| 2003/0162393 A1 | 8/2003 | Sato | |
| 2005/0017260 A1* | 1/2005 | Lee | 257/101 |
| 2005/0129947 A1* | 6/2005 | Peng et al. | 428/403 |
| 2006/0068506 A1* | 3/2006 | Uyeda et al. | 436/525 |
| 2006/0157720 A1* | 7/2006 | Bawendi et al. | 257/98 |
| 2009/0109435 A1 | 4/2009 | Kahen et al. | |
| 2010/0255487 A1* | 10/2010 | Beechem et al. | 435/6 |
| 2011/0003343 A1* | 1/2011 | Nikiforov et al. | 435/91.5 |

FOREIGN PATENT DOCUMENTS

| | | |
|---|---|---|
| EP | 1762642 B1 | 8/2011 |
| KR | 10-2007-0029915 | 3/2007 |
| WO | WO-99/26299 | 5/1999 |
| WO | WO-2008/090814 | 7/2008 |
| WO | WO-2008/090814 A1 | 7/2008 |
| WO | WO-2009026396 | 2/2009 |
| WO | WO-2009/058173 | 5/2009 |
| WO | WO-2010/039897 | 4/2010 |
| WO | WO-2010/040074 | 4/2010 |
| WO | WO-2010/040111 | 4/2010 |
| WO | WO-2010/096084 | 8/2010 |

OTHER PUBLICATIONS http://www.lifetechnologies.com/us/en/home/references/molecular-probes-the-handbook/ultrasensitive-detection-technology/qdot-nanocrystal-technology.html, from The Molecular Probes Handbook, Section 6.6, pp. 3 and 4 of the pdf file, printed Sep. 10, 2014.*

Xie et al., Synthesis and Characterization of Highly Luminescent CdSe-Core CdS/Zn0.5Ce0.5S/ZnS Multishell Nanocrystals, published on the web, Apr. 29, 2005, J. Am. Chem. Soc., vol. 127, pp. 7480-7488.*

Tsay et al., "Enhancing the Photoluminescence of Peptide-Coated Nanocrystals with Shell Composition and UV Irradiation", published on web Jan. 12, 2005, J. Phys. Chem. B, vol. 109, pp. 1669-1674.*

Hohng, S. et al., "Near-complete suppression of quantum dot blinking in ambient conditions", *J Am Chem Soc*, 126, 2004, pp. 1324-1325.

Wang, X et al., "Non-blinking semiconductor nanocrystals", *Nature* 459, 2009, pp. 686-689.

Yao, J. et al., "Blinking and nonradiant dark fraction of water-soluble quantum dots in aqueous solution", *Proc Natl Acad Sci U S A*, 102, 2005, pp. 14284-14289.

Bruchez, Marcel P. et al., "Luminescent Semiconductor Nanocrystals: Intermitten Behaviour and Use as Fluorescent Biological Probes", *UMI Disseratation Information Service*, 1998, 1-115.

Dameron, C. et al., "Characterization of Peptide-Coated Cadmium-Sulfide Crystallites", *Inorg Chem*, 1990, 1343-1348.

Kratysberg, et al., *Methods* 46 (4), 2008, 269-73.

Mahler, B. et al., "Towards non-blinking colloidal quantum dots", *Nature Materials*, vol. 7, 2008, pp. 659-664.

PCT/US09/61951, International Preliminary Report on Patentability Mailed May 5, 2011.

PCT/US09/61953, International Preliminary Report on Patentability Mailed May 5, 2011.

Rajh, Tijana et al., "Synthesis and Characterization of Surface-Modified Colloidal CdTe Quantum Dots", *J Phys Chem*, vol. 97, No. 46, 1993, 11999-12003.

Wang, X et al., "Non-Blinking Semiconductor Nanocrystals", *nature letters*, 459, 2009, 686-689.

Weller, H., "Optical Properties of Quantized Semiconducotr Particles", *Philosophical Transaction: Mathematical, Physical and Engineering Sciences*, vol. 354, No. 1708, 1996, 757-766.

Xie, R. et al., "Synthesis and Characterization of Highly Luminescent CdSe-Core CdS/Zn0.5Cd0.5S/ZnS Multishell Nancrystals.", *J. Am. Chem. Soc.*. 127, 2005, 7480-7488.

Casper, J., et al. "Photochemistry of tris (2,2'-bipyridine)ruthenium(2+) ion (Ru(bpy)32+). Solvent effects." *J. Am. Chem. Soc.*, 1983, 105 (17), pp. 5583-5590.

Dabbousi, B., et al. "(CDSE)ZnS Core—Shell Quantum Dots: Synthesis and Characterization of a Size Series of Highly Luminescent Nanocrystallites", *Journal of Physical Chemistry*, 1997, 107, pp. 9463-9475.

Embden, J., et al. "Review of the Synthetic Chemistry Involved in the Production of Core/Shell Semiconductor Nanocrystals." *Aust. J. Chem.* 2007, 60, pp. 457-471.

Hines, M., et al. "Synthesis and Characterization of Strongly Luminescing ZnS-Capped CdSe Nanocrystals", *J. Phys. Chem.* 1996, 100 ( 2), pp. 468-471.

Kuno, M., et al. "The Band Edge Luminescence of Surface Modified CdSe Nanocrystallites: Probing the Luminescing State" *Journal of Chemical Physics*; 1997, 106 (23), pp. 9869-9882.

Lakowicz, J. R. "Principles of Fluorescence Spectroscopy", 2nd Ed. Plenum Publishing Corp. New York, NY 1999, 367-394.

Muschielok, A., et al. "A Nano-Positioning System for Macromolecular Structural Analysis." *Nat. Methods*; 2008, 5 (11) pp. 965-971.

Nirmal, M., et al. "Fluorescence Intermittency in Single Cadmium Selenide Nanocrystals", *Nature*; 1996, 383, pp. 802-804.

International Search Report and Written Opinion for PCT Application No. PCT/US2009/061951 mailed on May 25, 2010.

International Search Report and Written Opinion for PCT Application No. PCT/US2009/061953 mailed May 25, 2010.

Peng, X., et al. "Epitaxial Growth of Highly Luminescent Cdse/cdS core/ Shell Nanocrystals with Photostability and Electronic Accessibilty", *J. Am. Chem. Soc.*, 1997, (119), pp. 7019-7029.

Piston, D., et al. "Fluorescent Protein FRET: the Good, the Bad and the Ugly", *Trends Biochem. Sci*.,2007, 32 (9), pp. 407-414.

Qu, L., et al. "Alternative Routes Toward High Quality CdSe Nanocrystals", *Nano Letters*, 2001, 1 (6), pp. 333-337.

Rogach, A., et al. "Synthesis and Characterization of Thiol-Stabilized CdTe nanocrystals." *Ber. Bunsenges. Phys. Chem.*, 1996, 100 (11), pp. 1772-1778.

Wozniak, A., et al. "Single-Molecule FRET Measures Bends and Kinks in DNA." *Proc. Natl. Acad. Sci. U.S.A.*, 2008; 105 (47), pp. 18337-18342.

* cited by examiner

Blinking of 605 Rods and 605 Spheres

(a) 605 Rods

| | |
|---|---|
| % always on | 37% +/- 4% |
| Median alpha on | 1.28 +/- 0.2 |
| Median % on time | 90% +/- 4% |

(b) CdSe/4CdS-3.5ZnS Spheres

| | |
|---|---|
| % always on | 77% +/- 4% |
| Median alpha on | always on |
| Median % on time | always on |

STABLE NANOPARTICLES AND METHODS OF MAKING AND USING SUCH PARTICLES

CROSS-REFERENCE TO RELATED APPLICATIONS

This application is a national stage filing of International Application No. PCT/US2009/061953, filed Oct. 23, 2009, which claims the benefit under 35 U.S.C. §119 (e) of U.S. Provisional Application Ser. No. 61/108,425 filed Oct. 24, 2008, and U.S. Provisional Application Ser. No. 61/144,613, filed Jan. 14, 2009. The disclosures of the above-identified applications are hereby incorporated by reference as if set forth in full.

TECHNICAL FIELD

This application relates to small and stable nanoparticles that are useful in a variety of fields including biology, analytical and combinatorial chemistry, medical diagnostics, genetic analysis, solar energy conversion, displays, and single molecule spectroscopy; and methods for their preparation and use.

BACKGROUND

Nanoparticles that fluoresce when excited by an appropriate energy source, such as a laser are powerful detection tools in a variety of life science applications ranging from Western blot detection of proteins, visualization of cell migration, flow cytometric analysis to in vivo imaging. Such nanoparticles also form foundational components in LEDs, solar cells, transistors, and diode lasers. However, the fluorescent nanoparticles currently available suffer from intermittent fluorescence or a stochastic blinking on and off of their fluorescence when the nanoparticles are excited. This blinking on and off limits the robustness of the signal as both the timing and duration of the on/off periods are unpredictable. For single particle or single molecule analysis, the blinking properties limit the usefulness of the fluorescent nanoparticles. Similarly, blinking results in significant hurdles (that can be insurmountable) in ultra high-throughput applications using a population of nanoparticles, due to unpredictable variations in signal intensity resulting from the nanoparticles intermittently toggling between an on/off state.

While not being bound to a particular theory, one premise attributes the blinking behavior to the steep electronic interface between the particle and the "outside world." Blinking therefore may result from the temporary loss of a photoelectron or Auger electron (or a hole) from the particle core to the surrounding matrix, for example by Auger ejection or charge tunneling, or to electron capture by surface-related traps, producing a charged state. When the nanoparticle is in a charged state, emission is turned off. Once charge neutrality is restored, emission turns on, resulting in the characteristic blinking. A key observation driving these theories is that blinking worsens as a function of excitation power. In other words, as the excitation power increases, the blinking typically increases as well. Such observations suggest that blinking occurs with either simultaneous or sequential excitation by two or more photons per excited state. Thus, one useful approach to suppress blinking can be to prevent electrons from escaping the particle core during or following a multiphoton event.

There is a need to develop approaches to provide small (such that they are useful in fluorescence resonance energy transfer applications) and stable nanoparticles which address the problems posed by nanoparticle fluorescent intermittency (as this intermittency complicates the reliable use of "blinking" nanoparticles as a single photon light source for quantum informatics and as biolabels for real-time monitoring of single biomolecules).

SUMMARY

Provided herein are nanocrystals that are water-soluble or dispersable, and are also bright, with modulated, reduced or no intermittent (e.g., continuous, non-blinking) fluorescence, and chemically and photochemically stable. Further provided are methods for producing a nanoparticle and populations thereof with modulated, reduced or no fluorescence intermittency or "blinking", and methods of using them. The compositions and methods disclosed herein may be useful for various biological applications, including, but not limited to: cell staining, cell tracking, in vivo imaging, in vitro imaging, blots, flow cytometry, FISH, DNA sequencing and other biological applications.

In one aspect, a population of nanoparticles is disclosed. The population is comprised of a plurality of core/shell nanocrystals, each including: a semiconductor core, an intermediate semiconductor shell layer disposed over the semiconductor core, an external semiconductor shell layer disposed over the intermediate semiconductor shell layer, and a hydrophilic organic layer in direct contact with the external semiconductor shell layer. The population of nanoparticles has a $\alpha_{on}$ value of less than about 1.4.

In another aspect, a method for producing a population of nanoparticles, is disclosed. A mixture including a plurality of nanocrystal cores and at least one coordinating solvent is provided. A first intermediate shell precursor is added alternately with a second intermediate shell precursor in layer additions to form an intermediate shell layer on each of the plurality of nanocrystal core. A first external shell precursor is added alternately with a second external shell precursor in layer additions to form an external shell layer on each of the plurality of nanocrystal cores. An aqueous solution comprising hydrophilic ligands is added. The mixture is maintained under conditions that cause the plurality of nanocrystals to migrate into an aqueous phase, wherein the resulting population of nanoparticles has a $\alpha_{on}$ value of less than about 1.4.

In another aspect, a method for producing a population of FRET capable nanoparticles, is disclosed. A mixture comprising a plurality of nanocrystal cores and at least one coordinating solvent is provided. A first intermediate shell precursor is added alternately with a second intermediate shell precursor in layer additions to form an intermediate shell layer on each of the plurality of nanocrystal cores, wherein the intermediate shell layer is comprised of more than one monolayer. A first external shell precursor is added alternately with a second external shell precursor in layer additions to form an external shell layer on each of the plurality of nanocrystal cores, wherein the external shell layer is disposed on top of the intermediate shell layer and is comprised of more than one monolayer. An aqueous solution comprising hydrophilic ligands is added. The mixture is maintained under conditions that cause the plurality of nanocrystals to migrate into an aqueous phase, wherein, the population of FRET capable nanoparticles has a FRET efficiency of greater than about 20%.

In another aspect, a method for producing a population of nanoparticles, is disclosed. A mixture comprising a plurality of nanocrystal cores, hydrophilic ligands and at least one coordinating solvent is provided. A first intermediate shell precursor is added alternately with a second intermediate shell precursor in layer additions to form an intermediate shell layer on each of the plurality of nanocrystal cores. A first external shell precursor is added alternately with a second external shell precursor in layer additions to form an external shell layer on each of the plurality of nanocrystal cores, wherein the resulting population of nanoparticles has a $\alpha_{on}$ value that is less than about 1.4.

These and other features, aspects, and embodiments are described below in the section entitled "Detailed Description."

BRIEF DESCRIPTION OF THE DRAWINGS

For a more complete understanding of the principles disclosed herein, and the advantages thereof, reference is now made to the following descriptions taken in conjunction with the accompanying drawings, in which.

DETAILED DESCRIPTION

Figure 1A:
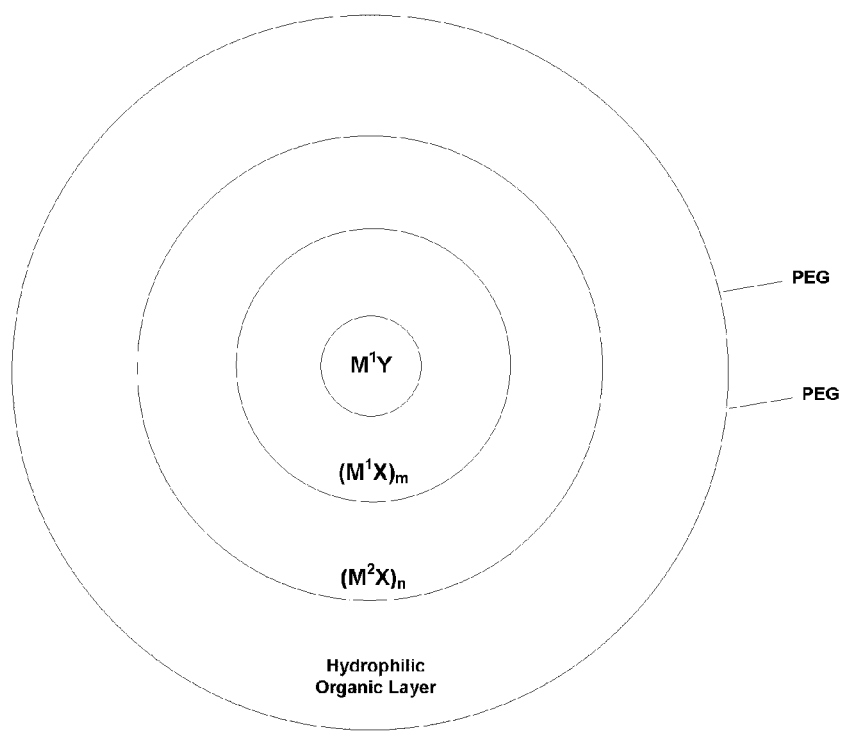
FIG. 1A is an illustration of a nanoparticle comprising a core ($M^1Y$) and a layered shell, wherein the shell comprises m inner shell monolayers comprising a first shell material ($M^1X$) and n outer shell monolayers comprising a second shell material ($M^2X$), in accordance with one embodiment.

The embodiments described herein may be understood more readily by reference to the following detailed description of the embodiments and the Examples included herein. It is to be understood that the terminology used herein is for the purpose of describing specific embodiments only and is not intended to be limiting.

Unless defined otherwise, all technical and scientific terms used herein have the same meaning as is commonly understood by one of ordinary skill in the art.

As used herein, "a" or "an" means "at least one" or "one or more."

As used herein, "about" means that the numerical value is approximate and small variations would not significantly affect the use and practice of the compositions and methods provided herein. Where a numerical limitation is used, unless indicated otherwise by the context, "about" means the numerical value can vary by ±10% and remain within the scope of the disclosed embodiments.

"Nanoparticle" as used herein refers to any particle with at least one major dimension in the nanosize range. Typically, a nanoparticle has at least one major dimension ranging from about 1 nm to about 1000 nm.

Examples of nanoparticles include a nanocrystal, such as a core/shell nanocrystal, plus any tightly-associated organic coating or other material that may be on the surface of the nanocrystal. A nanoparticle may also include a bare core/shell nanocrystal, as well as a core nanocrystal or a core/shell nanocrystal having a layer of, e.g., trioctylphosphine (TOP), trioctylphosphine oxide (TOPO), oleic acid, octylphosphonic acid (OPA), tetradecylphosphonic acid (TDPA) or other material that is not removed from the surface by ordinary solvation. A nanoparticle can have a layer of ligands on its surface which can further be cross-linked; and a nanoparticle can have other or additional surface coatings that can modify the properties of the particle, for example, increasing or decreasing solubility in water or other solvents. Such layers on the surface are included in the term 'nanoparticle.' In one embodiment, it can refer to a nanoparticle having a crystalline core, or to a core/shell nanocrystal, and may be about 1 nm to about 100 nm in its largest dimension, about 1 nm to about 20 nm, about 1 nm to about 15 nm, about 1 nm to about 10 nm, or preferably about 5 nm to about 10 nm in its largest dimension. Small nanoparticles are typically less than 20 nm in their largest dimension.

"Nanocrystal" as used herein can refer to a nanoparticle made out of an inorganic substance that typically has an ordered crystalline structure. It can refer to a nanocrystal having a crystalline core (core nanocrystal), or to a core/shell nanocrystal. Typically, a nanocrystal has a core diameter ranging from 1-100 nm in its largest dimension.

A core nanocrystal is a nanocrystal to which no shell has been applied; typically it is a semiconductor nanocrystal, and typically it is made of a single semiconductor material. It can have a homogeneous composition, or its composition can vary with depth inside the nanocrystal. Many types of nanocrystals are known, and any suitable method for making a nanocrystal core and applying a shell to the core may be employed. Nanocrystals generally require a surface layer of ligands to protect the nanocrystal from degradation in use or during storage.

"Quantum dot" as used herein refers to a nanocrystalline particle made from a material that in the bulk is a semiconductor or insulating material, which has a tunable photophysical property in the near ultraviolet (UV) to far infrared (IR) range.

"Water-soluble" or "aqueous-dispersable" is used herein to mean the item can be soluble or suspendable in an aqueous-based solution, such as in water or water-based solutions or buffer solutions, including those used in biological or molecular detection systems as known by those skilled in the art. While water-soluble nanoparticles are not truly 'dissolved' in the sense that term is used to describe individually solvated small molecules, they are solvated (via hydrogen, electrostatic or other suitable physical/chemical bonding) and suspended in solvents that are compatible with their outer surface layer, thus a nanoparticle that is readily dispersed in water is considered water-soluble or water-dispersible. A water-soluble nanoparticle can also be considered hydrophilic, since its surface is compatible with water and with water solubility.

"Hydrophobic nanoparticle" as used herein refers to a nanoparticle that is readily dispersed in or dissolved in a water-immiscible solvent like hexanes, toluene, and the like. Such nanoparticles are generally not readily dispersed in water.

"Hydrophilic" as used herein refers to a surface property of a solid, or a bulk property of a liquid, where the solid or liquid exhibits greater miscibility or solubility in a high-dielectric medium than it does in a lower dielectric medium. By way of example, a material that is more soluble in methanol than in a hydrocarbon solvent such as decane would be considered hydrophilic.

"Coordinating solvents" as used herein refers to a solvent such as TOP, TOPO, carboxylic acids, and amines, which are effective to coordinate to the surface of a nanocrystal. 'Coordinating solvents' also include phosphines, phosphine oxides, phosphonic acids, phosphinic acids, amines, and carboxylic acids, which are often used in growth media for nanocrystals, and which form a coating or layer on the nanocrystal surface. TOP and TOPO are sometimes preferred. Coordinating solvents exclude hydrocarbon solvents such as hexanes, toluene, hexadecane, octadecene, and the like, which do not have heteroatoms that provide bonding pairs of electrons to coordinate with the nanocrystal surface. Hydrocarbon solvents that do not contain heteroatoms such as O, S, N or P to coordinate to a nanocrystal surface are referred to herein as non-coordinating solvents. Note that the term 'solvent' is used in its ordinary way in these terms: it refers to a medium that supports, dissolves, or disperses materials and reactions between them, but which does not ordinarily participate in or become modified by the reactions of the reactant materials. However, in certain instances, the solvent can be modified by the reaction conditions. For example, TOP may be oxidized to TOPO, or a carboxylic acid can be reduced to an alcohol.

As used herein, the term "population" refers to a plurality of nanoparticles having similar physical and/or optical properties. "Population" can refer to a solution or structure with more than one nanoparticle at a concentration suitable for single molecule analysis. In some embodiments, the population can be monodisperse and can exhibit less than at least 15% rms deviation in diameter of the nanoparticles, and spectral emissions in a narrow range of no greater than about 75 nm full width at half max (FWHM). In the context of a solution, suspension, gel, plastic, or colloidal dispersion of nanoparticles, the nature of the population can be further characterized by the number of nanoparticles present, on average, within a particular volume of the liquid or solid, or the concentration. In a two-dimensional format such as an array of nanoparticles adhered to a solid substrate, the concept of concentration is less convenient than the related measure of particle density, or the number of individual particles per two-dimensional area. In this case, the maximum density would typically be that obtained by packing particles "shoulder-to-shoulder" in an array. The actual number of particles in this case would vary due to the size of the particles—a given array could contain a large number of small particles or a small number of larger particles. In the two-dimensional format the minimum density usually considered useful would be dependent on application, but typically would be around one particle per 10,000 square microns.

As used herein, the terms "moderate to high excitation" refers to monochromatic illumination or excitation (e.g., laser illumination) having a high power intensity sufficiently high such that the absorbed photons per second for a given sample is between about 200,000 and 1,600,000.

As used herein, fluorescence (or Forster) resonance energy transfer (FRET) is a process by which a fluorophore (the donor) in an excited state transfers its energy to a proximal molecule (the acceptor) by nonradiative dipole-dipole interaction (Forster, T. "Intermolecular Energy Migration and Fluorescence", *Ann. Phys.*, 2:55-75, 1948; Lakowicz, J. R., *Principles of Fluorescence Spectroscopy*, 2nd ed. Plenum, New York. 367-394, 1999).

FRET efficiency (E) can be defined as the quantum yield of the energy transfer transition, i.e. the fraction of energy transfer event occurring per donor excitation event. It is a direct measure of the fraction of photon energy absorbed by the donor that is transferred to an acceptor, as expressed in Equation 1:

$$E = k_{ET}/k_f + k_{ET} + \Sigma k_i \qquad \text{Eq. 1}$$

where $k_{ET}$ is the rate of energy transfer, $k_f$ the radiative decay rate and the $k_i$ are the rate constants of any other de-excitation pathway.

FRET efficiency E generally depends on the inverse of the sixth power of the distance r between the two fluorophores (i.e., donor and acceptor pair), as expressed in Equation 2:

$$E = 1/1 + (r/R_0)^6 \qquad \text{Eq. 2}$$

The distance where FRET efficiency is at 50% is termed $R_0$, also know as the Forster distance. $R_0$ can be unique for each donor-acceptor combination. Therefore, the FRET efficiency of a donor (i.e., nanoparticle) describes the maximum theoretical fraction of photon energy that is absorbed by the donor (i.e., nanoparticle) and that can then be transferred to a typical organic dye (e.g., fluoresceins, rhodamines, cyanines, etc.).

"Quantum yield" as used herein refers to the emission efficiency of a given fluorophore assessed by the number of times that a defined event, e.g., light emission, occurs per photon absorbed by the system. In other words, a higher quantum yield indicates greater efficiency and thus greater brightness of the described nanoparticle or populations thereof.

Any suitable method can be used to measure quantum yield. In one example, quantum yield can be obtained using standard methods such as those described in Casper et al (Casper, J. V.; Meyer, T. J. *J. Am. Chem. Soc.* 1983, 105, 5583) and can be analyzed relative to known fluorophores chosen as appropriate for maximal overlap between standard emission and sample emission (e.g., fluorescein, Rhodamine 6G, Rhodamine 101). Briefly, dilute solutions of the standard and sample can be matched or nearly matched in optical density prior to acquisition of absorbance and emission spectra for both. The emission quantum yield ($\phi_{em}$) then can be determined according to Equation 3:

$$\phi_{em} = \phi'_{em}\left(\frac{I}{I'}\right)\left(\frac{A'}{A}\right) \qquad \text{Eq. 3}$$

where A and A' are the absorbances at the excitation wavelength for the sample and the standard respectively and I and I' are the integrated emission intensities for the sample and standard respectively. In this case $\phi'_{em}$ can be the agreed upon quantum yield for the standard.

Disclosed herein are fluorescent nanoparticles with superior and robust properties that significantly expand the applications in which nanoparticles are useful. These nanoparticles are superior and surprisingly robust in that they are simultaneously stable, bright, and sensitive to environmental stimuli. Moreover, the disclosed nanoparticles have limited or no detectable blinking (i.e., where the nanoparticle emits light non-intermittently when subject to excitation), are highly photostable, have a consistently high quantum yield, are small (e.g., ≤20 nm) and can act as a donor that undergoes FRET with a suitable acceptor moiety (e.g., fluorescent dyes, etc.). The photostability of these nanoparticles is reflected in their exhibiting reduced or no photobleaching (i.e., fading) behavior when subjected to moderate to high intensity excitation for at least about 20 minutes. Additionally, the particles can remain substantially free from photo-induced color shifting Put another way, the nanoparticles can maintain a consistent spectral emission pattern (i.e., maintain the ability to fluoresce) even when exposed to a large quantity of photons (i.e., moderate to high intensity excitation) for a long period of time. This unique combination of characteristics makes these types of nanoparticles sensitive tools for single molecule analysis and other sensitive high throughput applications. Moreover, these properties make the nanoparticles particularly well suited for use as highly efficient donor fluorophores in energy transfer reactions such as FRET reactions (i.e., high FRET efficiency) or other reactions as well as applications that require or are enhanced by greater response to the environment.

Non-blinking Nanoparticle(s)

Thus, in one aspect, a fluorescent nanoparticle or populations thereof with modulated, reduced or no intermittent (e.g., continuous, non-blinking) fluorescence, is provided.

The nanoparticle(s) provided herein are surprisingly superior to previously known nanoparticles because, among other reasons, they exhibit modulated or non-blinking behavior (as opposed to conventional nanoparticles, which are described in the art as having on-time fractions of <0.20 in the best of conditions examined).

Without being bound to a particular theory, blinking or fluorescence intermittency may arise during the nanoparticle charging process when an electron is temporarily lost to the surrounding matrix (Auger ejection or charge tunneling) or captured to surface-related trap states. The nanoparticle is "on" or fluorescing when all of the electrons are intact and the particle is "neutral" and the particle is "off" or dark when the electron is lost and the particle is temporarily (or in some cases permanently) charged. It is important to note that the complete suppression of blinking may not necessarily be required and in some instances may not be desirable. Blinking that occurs on a timescale much shorter or much longer than the interrogation period for a particular assay has relatively little impact on the performance of the system. Thus, nanoparticles and nanoparticle populations having modulated blinking properties, where blinking occurs on a very short or very fast timescale relative to the assay interrogation periods are also useful and fall within the scope of the present disclosure. Localization of timescale or simply pushing timescale to one side (e.g., to where the blinking is undetectable within the assay system) provides enormous benefit in application development.

The blinking behavior of the nanoparticles described herein can be analyzed and characterized by any suitable number of parameters using suitable methodologies. In some embodiments, the probability distribution function of the "on" and "off" blinking time durations (i.e., blinking behavior) can be determined using the form of an inverse power law. A value, alpha ($\alpha$) can be calculated, wherein $\alpha$ represents an exponent in the power law. As the percentage of the population that is non-blinking increases, the value of $\alpha_{on}$ theoretically approaches zero. In conventional nanoparticle populations previously described, $\alpha_{on}$ typically ranges from about 1.5 to about 2.5, under moderate to high excitation energy.

Most alpha calculations can use a predetermined threshold to determine the "on" and "off" values of alpha-on and alpha-off (i.e., $\alpha_{on}$ and $\alpha_{off}$). In some embodiments, an alpha estimator that calculates the on/off threshold for each dot individually can be employed. The data can be represented by a plot of signal versus frequency, and typically appears as a series of Gaussian distributions around the "off state" and one or more "on states." A log-log plot of frequency versus time for each period of time that the dot is "on" provides a straight line having a slope of $\alpha_{on}$. The value of alpha-off ($\alpha_{off}$) can be similarly determined.

In a specific example (the "TIRF example"), the fluorescent intermittency measurements can be made using a Total Internal Reflection Fluorescence (TIRF) microscope fitted with a 60× oil immersion objective lens, using a dual view with a longpass filter on the acceptor side and a bandpass filter on the donor side. Using the TIRF setup, the nanoparticles were imaged at 30 Hz (33 ms), typically for 5 minutes, to produce a movie showing the time and intensity of the emitted light for each individual spot (corresponding to a single particle) within a binned frame that was 33 ms long; the intensity for each binned frame can be integrated. Each data set can be manually analyzed dot-by-dot, and aggregates and other artifacts were excluded. From the edited results, the following parameters can be calculated: alpha-on ("$\alpha_{on}$"); alpha-off ("$\alpha_{off}$"); the percent on; longest on/longest off; overlap scores; and the median values for each of these parameters.

In some embodiments, provided herein is a nanoparticle or population thereof that has an $\alpha_{on}$ of less than about 1.5, $\alpha_{on}$ of less than about 1.4, $\alpha_{on}$ of less than about 1.3, $\alpha_{on}$ of less than about 1.2, or an $\alpha_{on}$ of less than about 1.1, under moderate to high excitation energy. Further provided is a population of more than one nanoparticle wherein the at least about 50%, at least about 60%, at least about 70%, at least about 80%, at least about 90%, at least about 95%, at least about 98%, at least about 99% or more of the population has an $\alpha_{on}$ of less than about 1.5, $\alpha_{on}$ of less than about 1.4, $\alpha_{on}$ of less than about 1.3, $\alpha_{on}$ of less than about 1.2, or $\alpha_{on}$ of less than about 1.1 for the time observed, under moderate to high excitation energy. The observation time can be at least about 5 minutes, at least about 10 minutes, at least about 15 minutes, at least about 30 minutes, at least about 45 minutes, at least about 60 minutes, at least about 90 minutes, at least about 120 minutes or more under moderate to high excitation energy. Compositions comprising such a nanoparticle and populations thereof also are contemplated.

Also provided herein is a nanoparticle or a population thereof having a stochastic blinking profile that is either undetectable or rare (e.g., no more than 1-2 events during the interrogation period) over an observed timescale. In this case, "undetectable" encompasses the situation in which evidence might exist for ultra-fast blinking on a timescale that is faster than the binning timescale (e.g., dimming and brightening from bin to bin) but there are no "off" events persisting for longer than the bin time. Therefore, in some embodiments, a nanoparticle or populations thereof has a stochastic blinking profile that is undetectable for at least about 50%, at least about 60%, at least about 70%, at least about 80%, at least about 85%, at least about 90%, at least about 95%, at least about 98%, at least about 99% or more of the time observed, under moderate to high excitation energy. Further provided, is a population of nanoparticles wherein at least about 50%, at least about 60%, at least about 70%, at least about 80%, at least about 90%, at least about 95%, at least about 98%, at least about 99% or more of the individual nanoparticles in the population have a stochastic blinking on a timescale that is undetectable for the time observed, under moderate to high excitation energy. The timescale can be at least about 5 minutes, at least about 10 minutes, at least about 15 minutes, at least about 30 minutes, at least about 45 minutes, at least about 60 minutes, at least about 90 minutes, at least about 120 minutes or more under moderate to high excitation energy.

In some embodiments, the longest on and longest off values can relate to the longest period of time a nanoparticle is observed to be in either the "on" or the "off" state. In particular, the longest on value can be important to determining the length of time and amount of data that may be measured in a particular assay.

Thus, the blinking characteristics of the nanoparticles herein can also be characterized by their on-time fraction, which represents the (total on-time)/(total experiment time). Under the TIRF example disclosed herein, the total on time can be determined by the total number of frames "on" multiplied by 33 ms, and the total experiment time is 5 minutes. For example, the blinking properties of the disclosed nanoparticles or populations thereof can be determined under continuous irradiation conditions using a 405 nm laser with an intensity of about 1 watt per $cm^2$ during an experimental window of at least 5 minutes.

On-time fractions can be used to characterize the blinking behavior of a single nanoparticle or of a population of nanoparticles. It is important to note that the on-time fraction for a particular nanoparticle or population of nanoparticles is a function of the specific conditions under which the percent of blinking or "non-blinking" nanoparticles is determined. For example, the nanoparticles or populations described herein can have an on-time fraction of at least about 0.50, at least about 0.60, at least about 0.70, at least about 0.75, at least about 0.80, at least about 0.85, at least about 0.90, at least about 0.95, at least about 0.96, at least about 0.97, at least about 0.98, or at least about 0.99 or more, under moderate to high excitation energy. In some embodiments, a nanoparticle or populations thereof having a percent on-time of about 98%, about 99% (i.e., on-time fraction of about 0.99) can be considered to be "non-blinking." (e.g., blinking is modulated), under moderate to high excitation energy. At least about 50%, at least about 60%, at least about 70%, at least about 80%, at least about 90%, at least about 95%, at least about 98%, at least about 99%, or more of the individual nanoparticles in a population of nanoparticles can have an on-time fraction of at least about 0.50, at least about 0.60, at least about 0.70, at least about 0.75, at least about 0.80, at least about 0.85, at least about 0.90, at least about 0.95, at least about 0.96, at least about 0.97, at least about 0.98, or at least about 0.99 or more, under moderate to high excitation energy. The on-times of the nanoparticles are typically for at least about 5 minutes, at least about 10 minutes, at least about 15 minutes, at least about 20 minutes, at least about 30 minutes, at least about 45 minutes, at least about 60 minutes, at least about 70 minutes, at least about 80 minutes, at least about 90 minutes, at least about 120 minutes under moderate to high intensity excitation of the nanoparticle or nanoparticle population. Under one set of conditions, continuous irradiation with 405 nm laser with an approximate intensity of 1 watt per $cm^2$ was used to determine the stochastic blinking profile.

In some embodiments, nanoparticles which have a stochastic (i.e., random) blinking profile in a timescale that shifts from very rapid blinking or very slow/infrequent blinking (relative to a nanoparticle previously described in the art) can be considered to have modulated blinking properties. In some embodiments, these nanoparticles may blink on and off on a timescale that is too rapid to be detected under the methods employed to study this behavior. Thus, certain nanoparticles can effectively appear to be "always on" or to have on-time fractions of about 0.99, when in fact they flicker on and off at a rate too fast or too slow to be detected. Such flickering has relatively little impact on the performance of a system, and for practical purposes such nanoparticles can be considered to be non-blinking.

In some instances, the disclosed nanoparticles and populations thereof are not observed to blink off under the analysis conditions, and such particles can be assessed as "always on" (e.g., non-blinking). The percent of usable dots that are "always on" can be a useful way to compare nanoparticles or populations of nanoparticles. However, a determination of "always on" may mean that the "off" time was insufficient to provide enough a signal gap for accurate determination and thus the value in the regime of particles is insufficient to calculate. Even these "non-blinking" nanoparticles may flicker on and off on a timescale that is not detected under the conditions used to assess blinking. For example, certain particles may blink on a timescale that is too fast to be detected, or they may blink very rarely, and, in some embodiments, such particles may also be considered to be "always-on" or non-blinking, as the terms are used herein.

In some embodiments, a nanoparticle or populations thereof may demonstrate some fluctuation in fluorescence intensity. Typically, the change in fluorescence intensity for a nanoparticle is less than about 5%, less than about 10%, less than about 20%, or less than about 25% of the nanoparticle or populations thereof at its greatest intensity, under moderate to high excitation energy. Similarly, in a population of nanoparticles, such changes in fluorescence intensity of less than about 5%, less than about 10%, less than about 20%, or less than about 25% of the highest intensity can occur in for at least about 50%, at least about 60%, at least about 70%, at least about 80%, at least about 85%, at least about 90%, at least about 95%, at least about 98%, at least about 99% of the nanoparticles in the population, under moderate to high excitation energy.

In some embodiments, the on-time fraction of the disclosed nanoparticles does not decrease by more than about 15% upon irradiation at increased laser power. In other embodiments, the on-time fraction of the disclosed nanoparticles does not decrease by more than about 10% upon irradiation at increased laser power. For example, it has been observed that the on-time fraction of the disclosed nanoparticles do not decrease by more than about 10% as laser power is increased from about 200,000 absorbed photons per second to about 1,600,000 absorbed photons per second.

In some embodiments, the nanoparticles with modulated, reduced or no intermittent (e.g., continuous, non-blinking) fluorescence disclosed herein can comprise of a core and a layered gradient shell. In other embodiments, the nanoparticle(s) disclosed herein can be comprised of a nanocrystal core (e.g., CdSe, etc.), at least one inner (intermediate) shell layer (e.g., CdS, etc.), and at least one outer (external) shell layer (e.g., ZnS, etc.) (See FIGS. 1A and 1B). In some embodiments, the inner and/or outer shell layers are each comprised of two or more discrete monolayers of the same material. In some embodiments, the largest dimension of the disclosed nanoparticle(s) is less than about 15 nm.

In some embodiments, the disclosed nanoparticle(s) can further comprise a surface organic coating in direct contact with the external shell layer that can impart certain physical/chemical characteristics to the nanoparticle(s), protect the nanoparticle(s) from degradation and/or allow the nanoparticle(s) to bind to biomolecules. Such coatings may be made using any suitable techniques known in the art. See, e.g., U.S. Pat. Nos. 6,048,616, 5,990,479, 5,690,807, 5,505,928 and 5,262,357, as well as International Patent Publication No. WO 99/26299, published May 27, 1999.

In some embodiments, the disclosed nanoparticle(s) have surface coatings (in direct contact with the external layer) adding various functionalities that facilitate the nanoparticles being water-dispersable or soluble in aqueous solutions. There are a number of suitable surface coatings that can be employed to permit aqueous dispersibility of the described nanoparticles. For example, the nanoparticle(s) disclosed herein can be comprised of a core/shell nanocrystal that is coated directly or indirectly with lipids, phospholipids, fatty acids, polynucleic acids, polyethylene glycol (PEG), primary antibodies, secondary antibodies, antibody fragments, protein or nucleic acid based aptamers, biotin, streptavidin, proteins, peptides, small organic molecules (e.g., ligands), organic or inorganic dyes, precious or noble metal clusters. Specific examples of coatings can include, but are not limited to, amphiphilic polymer (AMP), bidentate thiols (e.g., dihydrolipoic acid (DHLA), etc.), tridentate thiols, dipeptides, functionalized organophosphorous compounds (e.g., phosphonic acids, phosphinic acids), etc. See PCT Application Serial No. PCT/US09/59117; PCT/US09/59409; PCT/US09/53018; and PCT/US09/59456 which are expressly incorporated herein by reference as if set forth in full.

In some embodiments, the tridentate thiols can be compounds of Formula I, II, III, IV, V, or VI as shown below, and the like.

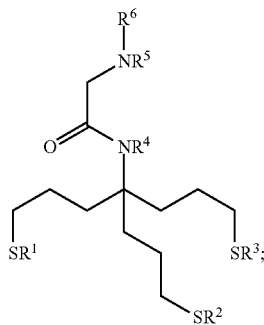

I

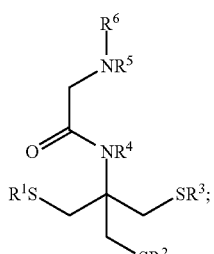

II

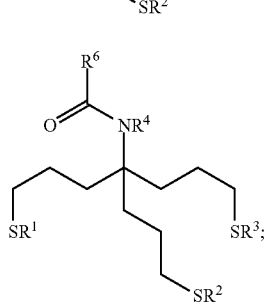

III

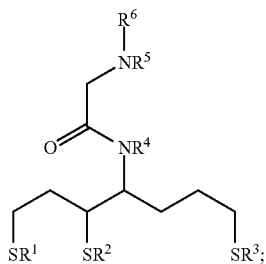

IV

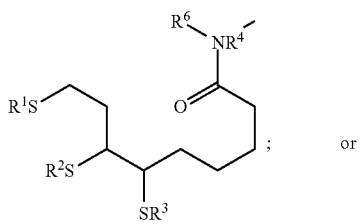

V or

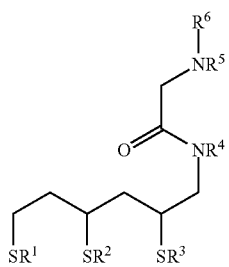

VI

In compounds of Formula I, II, III, IV, V, and VI, $R^1$, $R^2$, $R^3$ can independently be H, halo, hydroxyl, (—(C=O)—$C_1$-$C_{22}$, —(C=O)$CF_3$,) alkanoyl, $C_1$-$C_{22}$ alkyl, $C_1$-$C_{22}$ heteroalkyl, ((CO)O$C_1$-$C_{22}$) alkylcarbonato, alkylthio ($C_1$-$C_{22}$) or (—(CO)NH($C_1$-$C_{20}$) or —(CO)N($C_1$-$C_{20})_2$) alkylcarbamoyl. In some embodiments, $R^1$, $R^2$, and $R^3$ are different. In other embodiments, $R^1$, $R^2$, and $R^3$ are the same.

In compounds of Formula I, II, III, IV, V, and VI, $R^4$, and $R^5$ can independently be H, $C_1$-$C_{20}$ alkyl, $C_6$-$C_{18}$ aryl, $C_1$-$C_{22}$ heteroalkyl, or $C_1$-$C_{22}$ heteroaryl. In some embodiments, $R^4$ and $R^5$ are different. In other embodiments, $R^4$ and $R^5$ are the same.

In compounds of Formula I, II, III, IV, V, and VI, $R^6$ can be H or a polyethylene glycol based moiety of Formula VII:

VII

In certain embodiments of Formula VII, $R^7$ can be —$NH_2$, —$N_3$, —NHBoc, —NHFmoc, —NHCbz, —COOH, —COOt-Bu, —COOMe, iodoaryl, hydroxyl, alkyne, boronic acid, allylic alcohol carbonate, —NHBiotin, —(CO)NHNHBoc, —(CO)NHNHFmoc, or —OMe. In some embodiments, n can be an integer from 1 to 100.

In some embodiments, the functionalized organophosphorous ligands can be compounds of Formula VIII:

$(X)_n\text{-}(L\text{-}R)_y$ VIII wherein: each X can independently be a nanocrystal binding center selected from phosphonic acid, phosphinic acid, phosphine, and phosphine oxide; each L can independently be a linker selected from a covalent bond, saturated or unsaturated aliphatic chain of from 2 to about 500 carbon atoms, polyethylene glycol having from 2 to about 500 carbon atoms, or polyester having from 2 to about 100 carbon atoms; each R can independently be hydrogen or a functional group selected from halide, hydroxyl, carboxylic acid, carboxylic acid ester, ester, succinimidyl ester, alkyl ester, benzyl ester, aldehyde, amine including primary, secondary, or tertiary amine, polyamine, thiol, isocyanate, cycloalkyl, heterocycloalkyl, benzyl, aryl, heteroaryl, alkaryl, heterocycle, imidazole, pyridone, tetrazole, cyano, cyanoalkyl, thiol, thioalkyl, alkoxy, thioalkoxy, ether, alkyl ether, thioether, polyether, carbamates, azide, silyl, silyl ester, a polyethylene glycol moiety having from 2 to about 500 carbon atoms, a polyester having from 2 to about 20 carbon atoms, and combinations thereof; and y and n can independently be 1 to 3 with the proviso that when y is 1, R is not hydrogen and when y is 2 or 3, at least one R is not hydrogen.

In some embodiments, the nanoparticle(s) can be spherical or substantially spherical. In other embodiments, the nanoparticle(s) can be rod shaped or have a substantially elongated profile. In some embodiments, the disclosed nanoparticle(s) can have a quantum yield (i.e., ratio of photons emitted to photons absorbed) of greater than about 80%.

As discussed previously, the disclosed nanoparticle or population thereof is particularly well suited for use as a donor that undergoes FRET with a suitable acceptor moiety (e.g., fluorescent dyes, etc.). That is, the nanoparticles provided herein exhibit high FRET efficiency and thus are excellent partners (e.g., donors) in a FRET reaction. FRET refers to Florescence (or Förster) Resonance Energy Transfer, the basis of various fluorescence measuring techniques that allow detection of the close proximity of two molecules or species by assessing their interaction with one another. In a FRET reaction, a donor moiety can non-radiatively transfer energy to an acceptor moiety. The acceptor can be a chromophore or fluorophore which can then emit a photon. Donor-acceptor pairs are selected such that there is overlap between the emission spectrum of the donor and excitation spectrum of the acceptor. In some applications, the acceptor can also be a quencher. Therefore, a "FRET capable" nanoparticle can refer to a nanoparticle that can undergo a measurable FRET energy transfer event with an acceptor moiety.

FRET efficiency can depend sharply on donor-acceptor distance R as $1/R^6$. The distance where FRET efficiency is 50% is termed $R_0$, also known as the Forster distance. $R_0$ can be unique for each donor-acceptor combination and can range from about 5 nm to about 10 nm. In biological applications, FRET can provide an on-off type signal, indicating when the donor and acceptor are within $R_0$ of each other. Additional factors affecting FRET efficiency can include the quantum yield of the donor, the extinction coefficient of the acceptor, and the degree of spectral overlap between donor and acceptor. Extinction coefficient is essentially a measurement of a fluorophore's ability to absorb light on a per molar basis. Exemplary descriptions of FRET efficiency and signal detection can be found in D. W. Piston and G. J. Kremers, *Trends Biochem. Sci.* 32:407 (2007). In short, the overall size (diameter) of the nanoparticle can significantly impact the maximum theoretical limit of its FRET efficiency (i.e., FRET efficiency) with an acceptor moiety, based on the definitions established above. That is, the FRET efficiency of a nanoparticle can be impacted by the various characteristics of the nanoparticle itself, including, but not limited to: overall size, core/shell materials, external coatings, etc.

As such, in general, most FRET capable nanoparticles have a diameter that is than about 40 nm, less than about 30 nm, less than about 20 nm, and preferably less than about 15 nm.

Moreover, conventional nanoparticles were typically designed to maintain their fluorogenic properties in a microenvironment-independent manner. In other words, these nanoparticles were relatively inert (with respect to FRET interaction) to other fluorophores in their microenvironment by design to maximize the detection properties of the particles in the presence of naturally occurring fluorophores in blood and other solutions. In contrast, the disclosed nanoparticles can be exceptionally sensitive to microenvironmental stimuli and thus can be excellent partners in an energy transfer type reaction. The described nanoparticles can act as either a donor or acceptor in the reaction.

Thus, in one aspect, a FRET capable fluorescent nanoparticle or populations thereof with modulated, reduced or no intermittent (e.g., continuous, non-blinking) fluorescence, is provided.

In some embodiments, the FRET capable non-blinking fluorescent nanoparticle(s) disclosed herein can comprise a core and a layered gradient shell. In other embodiments, the FRET capable non-blinking nanoparticle(s) disclosed herein can be comprised of a nanocrystal core (e.g., CdSe, etc.), at least one inner (intermediate) shell layer (e.g., CdS, etc.), and at least one outer (external) shell layer (e.g., ZnS, etc.) (See FIGS. 1A and 1B). In some embodiments, the inner and/or outer shell layers are each comprised of two or more discrete monolayers of the same material. In some embodiments, the largest dimension of the disclosed nanoparticle(s) is less than about 15 nm.

In some embodiments, the disclosed FRET capable nanoparticle(s) can further comprise a surface organic coating in direct contact with the external shell layer that can impart certain physical/chemical characteristics to the nanoparticle(s), protect the nanoparticle(s) from degradation and/or allow the nanoparticle(s) to bind to biomolecules. Such coatings may be made using any suitable techniques known in the art. In some embodiments, the disclosed FRET capable nanoparticle(s) have surface coatings adding various functionalities that facilitate their being water-dispersable or soluble in aqueous solutions. There are a number of suitable surface coatings that can be employed to permit aqueous dispersibility of the described nanoparticles. For example, the nanoparticle(s) disclosed herein can be comprised of a core/shell nanocrystal that is coated directly or indirectly with lipids, phospholipids, fatty acids, polynucleic acids, polyethylene glycol (PEG), primary antibodies, secondary antibodies, antibody fragments, protein or nucleic acid based aptamers, biotin, streptavidin, proteins, peptides, small organic molecules (e.g., ligands), organic or inorganic dyes, precious or noble metal clusters. Specific examples of coatings can include, but are not limited to, bidentate thiols (i.e., DHLA), tridentate thiols, dipeptides, functionalized organophosphorous compounds (e.g., phosphonic acids, phosphinic acids), etc. In some embodiments, the selected surface organic coating makes the nanoparticles water soluble and have diameters of less than about 15 nm.

In some embodiments, the nanoparticle is the donor in a FRET reaction. Thus, provided herein is a nanoparticle or populations thereof with a FRET efficiency of at least about 20%, at least about 40%, at least about 50%, at least about 60%, at least about 70%, at least about 80%, at least about 90%, at least about 95%, at least about 98%, at least about 99%, or greater. A FRET capable nanoparticle is one that has at least about 25% efficiency in a FRET reaction.

In some embodiments, provided herein is a population of nanoparticles where at least about 30%, at least about 40%, at least about 50%, at least about 60% at least about 70%, at least about 80%, at least about 90%, at least about 95%, at least about 98%, at least about 99% or more of the individual nanoparticles in the population have a FRET efficiency of at least about 20%, at least about 40%, at least about 50%, at least about 60%, at least about 70%, at least about 80%, at least about 90%, at least about 95%, at least about 98%, at least about 99% or more. It should be understood that FRET efficiency can be determined by a variety of different methods including the ones disclosed above.

In some embodiments, the FRET efficiency of the disclosed nanoparticle or populations thereof can be maintained for at least about the first 10%, at least about the first 20%, at least about the first 30%, at least about the first 40%, at least about the first 50%, at least about the first 60%, at least about the first 70%, at least about the first 80%, at least about the first 90% or more of the total emitted photons under conditions of moderate to high excitation.

As discussed above, the nanoparticles provided herein can be considered to be surprisingly photostable. In particular, the nanoparticle and populations described herein can be photostable over an extended period of time while maintaining the ability to effectively participate in energy transfer (i.e., FRET) reactions. The disclosed nanoparticles are stable under high intensity conditions involving prolonged or continuous irradiation over an extended period of time from a moderate to high excitation source.

Thus, in one aspect, provided herein is a non-blinking fluorescent nanoparticle and populations thereof that are photostable.

In some embodiments, the photostable non-blinking fluorescent nanoparticle(s) disclosed herein can be comprised of a core and a layered gradient shell. In other embodiments, the photostable non-blinking nanoparticle(s) disclosed herein can be comprised of a nanocrystal core (e.g., CdSe, etc.), at least one inner (intermediate) shell layer (e.g., CdS, etc.), and at least one outer (external) shell layer (e.g., ZnS, etc.) (See FIGS. 1A and 1B). In some embodiments, the inner and/or outer shell layers are each comprised of two or more discrete monolayers of the same material.

In some embodiments, the disclosed photostable nanoparticle(s) can further be comprised of a surface organic coating in direct contact with the external shell layer that can impart certain physical/chemical characteristics to the nanoparticle(s), protect the nanoparticle(s) from degradation and/or allow the nanoparticle(s) to bind to biomolecules. Such coatings can be made using any suitable techniques known in the art. In some embodiments, the disclosed photostable nanoparticle(s) have surface coatings (in direct contact with the external shell layer) adding various functionalities that facilitate their being water-dispersable or soluble in aqueous solutions. There are a number of suitable surface coatings that can be employed to permit aqueous dispersibility of the described nanoparticles. For example, the nanoparticle(s) disclosed herein can comprise a core/shell nanocrystal that is coated directly or indirectly with lipids, phospholipids, fatty acids, polynucleic acids, polyethylene glycol (PEG), primary antibodies, secondary antibodies, antibody fragments, protein or nucleic acid based aptamers, biotin, streptavidin, proteins, peptides, small organic molecules (e.g., ligands), organic or inorganic dyes, precious or noble metal clusters. Specific examples of coatings can include, but are not limited to, amphiphilic polymer (AMP), bidentate thiols (i.e., DHLA), tridentate thiols, dipeptides, functionalized organophosphorous compounds (e.g., phosphonic acids, phosphinic acids), etc.

In some embodiments, the disclosed photostable nanoparticle and populations thereof can have an emitted light or energy intensity sustained for at least about 10 minutes and does not decrease by more than about 20% of maximal intensity achieved during that time. Further, these nanoparticles and populations thereof can have a wavelength spectrum of emitted light that does not change more than about 10% upon prolonged or continuous exposure to an appropriate energy source (e.g. irradiation).

In one embodiment, the photostable nanoparticles disclosed herein can remain photostable under moderate to high intensity excitation from at least about 10 minutes to about 2 hours. In another embodiment, the photostable nanoparticles disclosed herein can remain photostable under moderate to high intensity excitation from at least about 10 minutes to about 10 hours. In still another embodiment, the photostable nanoparticles disclosed herein can remain photostable under moderate to high from about 10 minutes to about 48 hours. However, it should be appreciated, that these are just example photostable times for the disclosed nanoparticles, in practice the nanoparticles can remain photostable for longer periods of time depending on the particular application.

It should be appreciated that nanoparticles that are photostable over longer timescales in combination with moderate to high excitation energy sources are well suited for more sensitive and broad-ranging applications such as the real-time monitoring of single molecules involving FRET. That is, the nanoparticle and populations thereof described herein can be photostable over an extended period of time while maintaining the ability to effectively participate in energy transfer (i.e., FRET) reactions, which makes the subject nanoparticles particularly useful for many applications involving the real-time monitoring of single molecules. As such, in some embodiments the photostable nanoparticles disclosed herein have FRET efficiencies of at least about 20%.

In some embodiments, the described nanoparticles are stable upon prolonged or continuous irradiation (under moderate to high excitation rate) in that they do not exhibit significant photo-bleaching on the timescales indicated. Photobleaching can result from the photochemical destruction of a fluorophore (and can be characterized by the nanoparticles losing the ability to produce a fluorescent signal) by the light exposure or excitation source used to stimulate the fluorescence. Photobleaching can complicate the observation of fluorescent molecules in microscopy and the interpretation of energy transfer reactions because the signals are destroyed or diminished increasingly as timescales for the experiment increase or the energy intensity increases.

Photobleaching can be assessed by measuring the intensity of the emitted light or energy for a nanoparticle or nanoparticle population using any suitable method. Typically, for the described nanoparticle or populations thereof, the intensity of emitted light or energy does not decrease more than about 20% (and in some embodiments, not more than about 10%) upon prolonged or continuous irradiation (under moderate to high excitation rate) of the nanoparticle and populations thereof. Sometimes, the intensity of emitted light does not decrease by more than about 20%, about 15%, about 10%, about 5% or less upon irradiation from about 10 minutes, about 20 minutes, about 30 minutes, about 45 minutes, about 60 minutes, about 90 minutes, about 2 hours, about 3 hours to about 4 hours, under moderate to high excitation energy.

In some embodiments, the photostable nanoparticles provided herein further demonstrate enhanced stability in that they exhibit a reduction in or absence of spectral shifting during prolonged excitation. In the nanoparticles previously described in the art, increased exposure to an excitation source—whether via increase time or power—results in a spectral shift of the wavelength emission wavelength profile of a nanoparticle and populations thereof from a longer wavelength to an increasingly shorter wavelength. Such spectral shifting of emission wavelength represents a significant limitation as precise resolution of emission spectra is required for applications that require rapid detection, multi-color analysis, and the like. Shifting of any significance then requires that the wavelength emissions used in an assay be sufficiently separated to permit resolution, thus reducing the number of colors available as well as increasing signal to noise ratio to an unacceptable level as the initial spectral profile cannot be relied upon once spectral shifting begins. Such shifting requires shortened observation times or use of fluorophores with widely separated emission spectra. The nanoparticles provided herein have little to no spectral shift, particularly over extended periods of excitation.

Wavelength emission spectra can be assessed by any suitable method. For example, spectral characteristics of nanoparticles can generally be monitored using any suitable light-measuring or light-accumulating instrumentation. Examples of such instrumentation are CCD (charge-coupled device) cameras, video devices, CIT imaging, digital cameras mounted on a fluorescent microscope, photomultipliers, fluorometers and luminometers, microscopes of various configurations, and even the human eye. The emission can be monitored continuously or at one or more discrete time points. The photostability and sensitivity of nanoparticles allow recording of changes in electrical potential over extended periods of time.

Thus, in some embodiments, the disclosed photostable nanoparticle and populations thereof have a wavelength spectrum of emitted light that does not change more than about 10% upon prolonged or continuous exposure to an appropriate energy source (e.g. irradiation) over about 4 minutes to about 10 minutes, under moderate to high excitation energy. In other embodiments, the wavelength emission spectra does not change more than about 5%, more than about 10%, more than about 20% over 10 minutes, about 20 minutes, about 30 minutes, about 45 minutes, about 60 minutes, about 90 minutes, about 2 hours, about 3 hours to about 4 hours.

It should be appreciated that there can be various other objective indicia of nanoparticle photostability. For example, a nanoparticle can be classified as photostable when the nanoparticle, under moderate to high excitation, emits about 1,000,000 to about 100,000,000 photons or more preferably about 100,000,001 to about 100,000,000,000 photons or even more preferably more than about 100,000,000,000 photons before becoming non-emissive (i.e., bleached).

A nanoparticle with modulated, reduced or no fluorescent intermittency (i.e., non-blinking); reduced or absent spectral shifting; low to no photobleaching; high quantum yield; and sufficient FRET efficiency can be of any suitable size. Typically, it is sized to provide fluorescence in the UV-visible portion of the electromagnetic spectrum as this range is convenient for use in monitoring biological and biochemical events in relevant media.

The disclosed nanoparticle and populations of such nanoparticles can have any combination of the properties described herein. Thus, in some embodiments the nanoparticle or populations thereof have modulated or no blinking, are photostable (e.g., limited or no photobleaching, limited or no spectral shift), have high quantum yield, have high FRET efficiency, have diameters of less than about 15 nm, are spherical or substantially spherical shape, or any combination of all these properties as described herein.

Likewise, in some embodiments, at least about 50%, at least about 60%, at least about 70%, at least about 80%, at least about 90%, at least about 95%, at least about 98%, at least about 99%, or more of the individual nanoparticles in a population of nanoparticles have modulated or no blinking, are photostable (e.g., limited or no photobleaching, limited or no spectral shift), have high quantum yield, have high FRET efficiency, have diameters of less than about 15 nm, are spherical or substantially spherical shape, or any combination of or all of these properties as described herein.

For some applications, the modulation or suppression of blinking may be balanced with the other characteristic properties of the nanoparticle that are important for the application of interest. Important characteristics to be considered in the overall engineering of a nanoparticle having modified blinking include, e.g., the particle size, quantum yield, chemical stability and photostability, and the relative sensitivity of the nanoparticle to the surrounding environment. Depending on the intended use, the relative advantage of a particular approach to suppressing blinking may be offset by, e.g., the loss of quantum yield, a decrease in particle stability, or an increase in particle size that makes the nanoparticle unsuitable for an intended purpose. For example, a nanoparticle that lacks sensitivity to its surrounding environment may not be useful as a FRET donor, regardless of its blinking characteristics, and a very large non-blinking nanoparticle may not be useful in certain in vivo applications that require small particle size.

The FRET capable, non-blinking and/or photostable nanoparticle(s) provided herein can be small, i.e., less than about 20 nm in their largest diameter when measuring the core/shell structure. In some embodiments, the nanoparticle(s) can be less than about 15 nm, less than about 10 nm, less than about 8 nm, less than about 6 nm, less than about 5 nm, less than about 4 nm, less than about 3 nm or less in its largest diameter when measuring the core/shell structure. Any suitable method may be used to determine the diameter of the nanoparticle(s). The nanoparticle(s) provided herein can be grown to the desired size using any of the methods disclosed herein. In some embodiments, at least about 50%, at least about 60%, at least about 70%, at least about 80%, at least about 90%, at least about 95%, at least about 98%, at least about 99%, or more of the individual members of a population of nanoparticles have maximum diameters (when measuring the core/shell structure) that are less than about 20 nm, less than about 15 nm, less than about 10 nm, less than about 8 nm, less than about 6 nm, less than about 5 nm, less than about 4 nm, less than about 3 nm or less.

The FRET capable, non-blinking and/or photostable nanoparticle(s) provided herein and populations thereof can be spherical or substantially spherical. In some embodiments, a substantially spherical nanoparticle can be one where any two radius measurements do not differ by more than about 10%, about 8%, about 5%, about 3% or less. In some embodiments, at least about 50%, at least about 60%, at least about 70%, at least about 80%, at least about 90%, at least about 95%, at least about 98%, at least about 99%, or more of the individual members of a population of nanoparticles are spherical or substantially spherical.

It should be understood that the nanoparticles disclosed herein can be synthesized in shapes of different complexity such as spheres, rods, discs, triangles, nanorings, nanoshells, tetrapods, nanowires and so on. Each of these geometries can have distinctive properties: spatial distribution of the surface charge, orientation dependence of polarization of the incident light wave, and spatial extent of the electric field. In some embodiments, the nanoparticles are substantially spherical or spheroidal, and comprise a thick, uniform, layered shell that is substantially free of defects. It should be noted, however, that nanoparticles of other shapes having a thick, uniform, layered shell are also possible.

For embodiments where the nanoparticle is not spherical or spheroidal, e.g. rod-shaped, it may be from about 1 to about 15 nm, from about 1 nm to about 10 nm, or 1 nm to about 5 nm in its smallest dimension. In some such embodiments, the nanoparticles may have a smallest dimension of about 0.5 nm, about 1 nm, about 2 nm, about 3 nm, about 4 nm, about 5 nm, about 6 nm, about 7 nm, about 8 nm, about 9 nm, about 10 nm, about 11 nm, about 12 nm, about 13 nm, about 14 nm, about 15 nm, about 16 nm, about 17 nm, about 18 nm, about 19 nm, about 20 nm, about 25 nm, about 30 nm, about 35 nm, about 40 nm, about 45 nm, about 50 nm and ranges between any two of these values.

In certain embodiments of single-color preparation of the nanoparticles disclosed herein can have individual nanoparticles that are of substantially identical size and shape. Thus, in some embodiments, the size and shape between the individual nanoparticles in a population of nanoparticles should vary by no more than about 20%, no more than about 15%, no more than about 10%, no more than about 8%, no more than about 6%, no more than about 5%, no more than about 4%, no more than about 3% or less in at least one measured dimension. In some embodiments, disclosed herein is a population of nanoparticles, where at least about 60%, at least about 70%, at least about 80%, at least about 90%, at least about 95%, and ideally about 100% of the particles are of the same size. Size deviation can be measured as root mean square ("rms") of the diameter, with the population having less than about 30% rms, preferably less than about 20% rms, more preferably less than about 10% rms. Size deviation can be less than about 10% rms, less than about 9% rms, less than about 8% rms, less than about 7% rms, less than about 6% rms, less than about 5% rms, less than about 3% rms, or ranges between any two of these values. Such a collection of particles is sometimes referred to as being a "monodisperse" population. One of ordinary skill in the art will realize that particular sizes of nanoparticles can be obtained as particle size distributions.

The color (emitted light) of a nanoparticle can be "tuned" by varying the size and composition of the particle. Nanoparticles as disclosed herein can absorb a wide spectrum of wavelengths, and emit a relatively narrow wavelength of light. The excitation and emission wavelengths are typically different, and non-overlapping. The nanoparticles of a monodisperse population may be characterized in that they produce a fluorescence emission having a relatively narrow wavelength band. Examples of emission widths (FWHM) include less than about 200 nm, less than about 175 nm, less than about 150 nm, less than about 125 nm, less than about 100 nm, less than about 75 nm, less than about 60 nm, less than about 50 nm, less than about 40 nm, less than about 30 nm, less than about 20 nm, and less than about 10 nm. The width of emission is preferably less than about 60 nm full width at half maximum (FWHM), or less than about 50 nm FWHM, and sometimes less than about 40 nm FWHM, less than about 30 nm FWHM or less than about 20 nm FWHM. The emitted light preferably has a symmetrical emission of wavelengths.

The emission maxima of the disclosed nanoparticle and populations thereof can generally be at any wavelength from about 200 nm to about 2,000 nm. Examples of emission maxima include about 200 nm, about 400 nm, about 600 nm, about 800 nm, about 1,000 nm, about 1,200 nm, about 1,400 nm, about 1,600 nm, about 1,800 nm, about 2,000 nm, and ranges between any two of these values.

The nanocrystal core and shell of the nanoparticles disclosed herein can be made of any suitable metal and non-metal atoms that are known to form semiconductor nanocrystals. Suitable semiconductor materials for the core and/or shell include, but are not limited to, ones including Group 2-16, 12-16, 13-15 and 14 element-based semiconductors such as ZnS, ZnSe, ZnTe, CdS, CdSe, CdTe, HgS, HgSe, HgTe, MgS, MgSe, MgTe, CaS, CaSe, CaTe, SrS, SrSe, SrTe, BaS, BaSe, BaTe, GaN, GaP, GaAs, GaSb, InP, InAs, InSb, AlAs, AlP, AlSb, PbS, PbSe, Ge and Si and ternary and quaternary mixtures thereof. Typically, the core and the shell of a core/shell nanocrystal are composed of different semiconductor materials, meaning that at least one atom type of a binary semiconductor material of the core of a core/shell is different from the atom types in the shell of the core/shell nanocrystal.

The disclosed nanoparticle can have a quantum yield (QY) of at least about 20%, at least about 40%, at least about 50%, at least about 60%, at least about 70%, at least about 80%, at least about 90%, at least about 95%, at least about 98%. In some embodiments, provided herein is a population of nanoparticles where at least about 30%, at least about 40%, at least about 50%, at least about 60%, at least about 70%, at least about 80%, at least about 90%, at least about 95%, at least about 98%, at least about 99% or more of the nanoparticles in the population has a QY of at least about 25%, at least about 40%, at least about 50%, at least about 60%, at least about 70%, at least about 80%, at least about 90%, at least about 95%, at least about 98%, at least about 99% or more.

Further provided herein are compositions comprising a population of nanoparticles, wherein at least about 10%, at least about 20%, at least about 30%, at least about 40%, at least about 50%, at least about 60%, at least about 70%, at least about 80%, at least about 90%, and at least about 95% of the nanoparticles have at least one of the properties or characteristics disclosed herein As discussed previously, the disclosed nanoparticle or populations thereof can comprise a core and a layered shell, wherein the shell includes at least one inner (intermediate) shell layer comprising a first shell material and at least one outer (external) shell layer comprising a second shell material, and wherein the layered shell is substantially uniform in coverage around the core and is substantially free of defects.

Figure 1B:
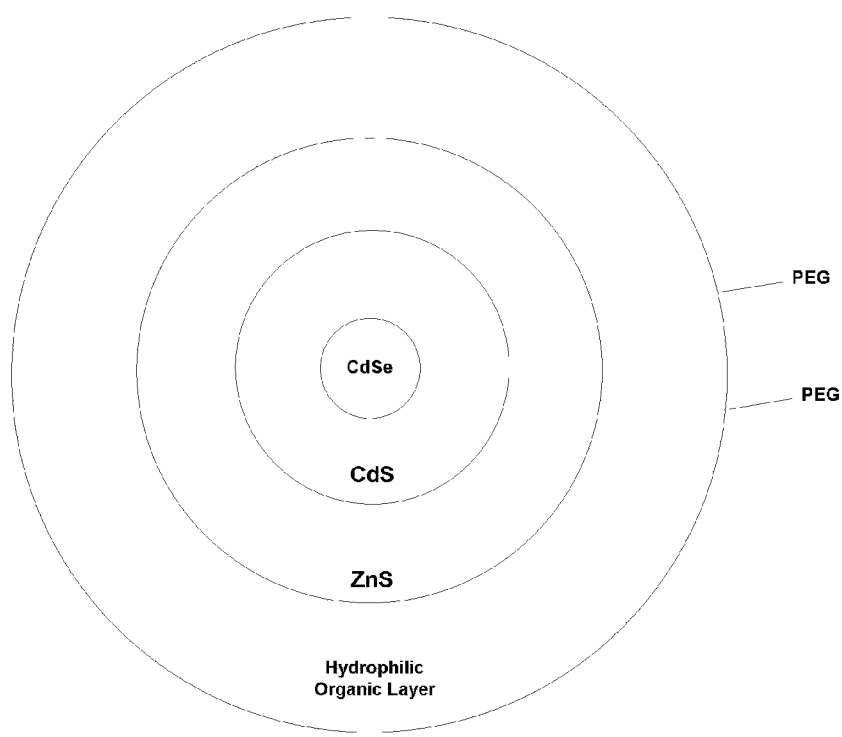
FIG. 1B is an illustration of a nanoparticle having a thick, uniform, layered shell, wherein the core comprises CdSe, the at least one inner shell layer comprises CdS, and the at least one outer shell layer comprises ZnS, in accordance with one embodiment.

Thus, in one aspect, the nanoparticle or populations thereof comprises a core ($M^1Y$) and a layered shell, wherein the shell comprises m inner shell monolayers comprising a first shell material $(M^1X)_m$ and n outer shell monolayers comprising a second shell material $(M^2X)_n$, wherein M can be a metal atom and X can be a non-metal atom, each of m and n is independently an integer from 1 to 10, and the layered shell is substantially uniform in coverage around the core and is substantially free of defects (See FIGS. 1A and 1B). In specific embodiments, the sum of m+n is 3-20, or 5-14, or 6-12, or 7-10.

In certain embodiments, the disclosed nanoparticles can further comprise one or more additional shell layers between the at least one inner shell layer and the at least one outer shell layer.

In some embodiments, the nanoparticle core and populations thereof can have a first bandgap energy and the first shell material can have a second bandgap energy, wherein the second bandgap energy can be greater than the first bandgap energy.

In a further aspect, provided herein is a nanoparticle comprising a core and a layered shell, wherein the shell comprises sequential monolayers comprising an alloyed multi-component shell material of the form $M^1_xM^2_yX$, where $M^1$ and $M^2$ can be metal atoms and X can be a non metal atom, where the composition becomes successively enriched in $M^2$ as the monolayers of shell material are deposited, where x and y represent the ratio of $M^1$ and $M^2$ in the shell material, and wherein the monolayered shell is substantially uniform in coverage around the core and is substantially free of defects. In some embodiments, the layered shell sometimes has about 3-20 monolayers of shell material, sometimes about 5-14 monolayers of shell material, sometimes about 6-12 monolayers of shell material, or sometimes about 7-10 monolayers of shell material.

In one aspect, provided herein is a nanoparticle comprising a core and a layered shell having a gradient potential, wherein the shell comprises at least one inner shell layer and at least one outer shell layer, and wherein the layered shell is substantially uniform in coverage around the core and is substantially free of defects.

The layered shell may be engineered such that the sequential monolayers are selected to provide a gradient potential from the nanoparticle core to the outer surface of the nanoparticle shell. The steepness of the potential gradient may vary depending on the nature of the shell materials selected for each monolayer or group of monolayers. For example, a nanoparticle comprising several sequential monolayers of the same shell material may reduce the potential through a series of steps, while a more continuous gradient may be achievable through the use of sequential monolayers of a multi-component alloyed shell material. In some embodiments, both single component and multi-component shell materials may be applied as different monolayers of a multi-layer shell on a nanoparticle.

The nanoparticles can be synthesized as disclosed to the desired size by sequential, controlled addition of materials to build and/or apply monolayers of shell material to the core. This is in contrast to conventional methods of adding shells where materials (e.g., diethylzinc and bis(trimethylsilyl)sulfide) are added together. Sequential addition permits the formation of thick (e.g., >2 nm) relatively uniform individual shells (e.g., uniform size and depth) on a core. The layer additions generally require the addition of an appropriate amount of the shell precursors to form a single monolayer, based on the starting size of the underlying core. This means that as each monolayer of shell material is added, a new "core" size must be determined by taking the previous "core" size and adding to it the thickness of just-added shell monolayer. This leads to a slightly larger volume of the following shell material needing to be added for each subsequent monolayer of shell material being added.

Each monolayer of shell material can be independently selected, and may be made up of a single component, or may comprise a multi-component (e.g., alloyed, etc.) shell material. In some embodiments, it is suitable to apply one or more sequential monolayers of a first shell material, followed by one or more sequential monolayers of a second shell material. This approach allows the deposition of at least one inner shell layer of a material having a bandgap and lattice size compatible with the core, followed by the deposition of at least one outer shell layer of a material having a bandgap and lattice size compatible with the inner shell layer. In some embodiments, multiple sequential monolayers of a single shell material can be applied to provide a uniform shell of a desired number of monolayers of a single shell material; in these embodiments, the first and second shell materials are the same. In other embodiments, sequential monolayers of an alloyed shell material are applied, where the ratio of the components varies such that the composition becomes successively enriched in one component of the multi-component mixture as the successive monolayers of shell material are deposited.

In some embodiments, the layered shell can be about 3-20 monolayers of shell material thick, sometimes about 5-14 monolayers of shell material thick, sometimes about 6-12 monolayers of shell material thick, or sometimes about 7-10 monolayers of shell material thick. In some embodiments, at least one inner shell layer can be comprised of about 3-5 monolayers, sometimes about 3-7 monolayers, of the first shell material. In other embodiments, at least one outer shell layer can be comprised of about 3-5 monolayers, sometimes about 3-7 monolayers, of the second shell material. In some embodiments, the inner shell layer can be at least 3 monolayers thick; in other embodiments, the outer shell layer can be at least 3 monolayers thick. The individual monolayers can be formed by the controlled, sequential addition of the layer materials methods described herein. The monolayers may not always be completely distinct as they may, in some embodiments, be a latticing between the surfaces of contacting monolayers.

In certain embodiments, provided herein are nanoparticles having a thick, uniform, layered shell, as described herein, wherein the core comprises CdSe, the at least one inner shell layer comprises CdS, and the at least one outer shell layer comprises ZnS (See FIG. 1B). In a particular embodiment, provided herein is a nanoparticle having a CdSe core and a layered shell comprising 4CdS+3.5ZnS layers. In some embodiments, provided herein is a nanoparticle that consists essentially of CdSe/4CdS-3.5ZnS. In some embodiments, provided herein is a nanoparticle that consists of CdSe/4CdS-3.5ZnS.

In some embodiments, the CdSe/4CdS-3.5ZnS nanoparticle has an on-time fraction of greater than about 0.80 (under moderate to high excitation energy); sometimes, the on-time fraction is greater than about 0.95 (under moderate to high excitation energy). In some such embodiments, the CdSe/4CdS-3.5ZnS nanoparticle has a quantum yield that is greater than about 50%, sometimes greater than about 60%, sometimes greater than about 70%, preferably greater than about 80% in organic solution, or greater than about 50% in aqueous solution.

In some embodiments, the disclosed nanoparticles can further comprise a coating in direct contact with the outer shell layer that permits the nanoparticle to be aqueous soluble and bind biomolecules. Such coatings may be made using any suitable techniques known in the art. See, e.g., U.S. Pat. Nos. 6,048,616, 5,990,479, 5,690,807, 5,505,928 and 5,262,357, as well as International Patent Publication No. WO 99/26299, published May 27, 1999. These methods typically produce nanocrystals having a coating of hydrophilic ligands on their surfaces which protect them from rapid degradation.

The nanoparticles above can have surface coatings (in direct contact with the outer shell layer) adding various functionalities that facilitate their being water-dispersable or soluble in aqueous solutions as well as to permit binding and/or other interaction with a biomolecule. Any suitable surface coating can be employed that permits aqueous dispersibility of the described nanoparticles. For example, the nanocrystals can be coated with lipids, phospholipids, fatty acids, polynucleic acids, polyethylene glycol, primary antibodies, secondary antibodies, antibody fragments, protein or nucleic acid based aptamers, biotin, streptavidin, proteins, peptides, small organic molecules (i.e., ligands), organic or inorganic dyes, precious or noble metal clusters. Specific examples of coatings can include, but are not limited to, amphiphilic polymer (AMP), bidentate thiols (i.e., DHLA), tridentate thiols, dipeptides, functionalized organophosphorous compounds (e.g., phosphonic acids, phosphinic acids), etc. See PCT Application Serial No. PCT/US09/59117; PCT/US09/59409; PCT/US09/53018; and PCT/US09/59456 which are expressly incorporated herein by reference as if set forth in full.

Methods of Making Non-blinking Nanoparticles

Disclosed herein are methods of making a nanoparticle and populations thereof with modulated, reduced or no fluorescence intermittency or "blinking". These nanoparticles can be small, photostable, bright, highly FRET efficient or some combination thereof. These nanoparticles can have a multi-shell layered core achieved by a sequential shell material deposition process, whereby one shell material is added at a time, to provide a nanoparticle having a substantially uniform shell of desired thickness that is substantially free of defects.

Figure 2:
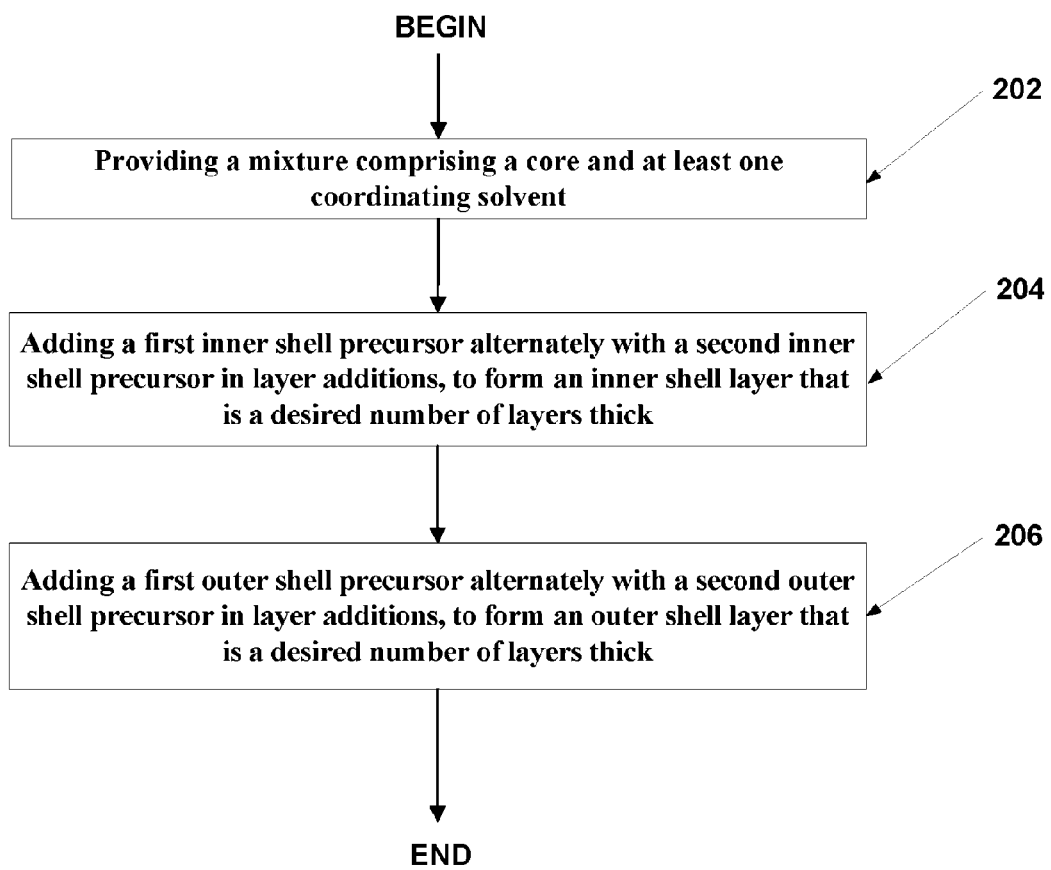
FIG. 2 is a process flowchart illustrating a method for making a non-blinking nanoparticle that is comprised of a core and a layered shell, wherein the shell is comprised of at least one inner shell layer and at least one outer shell layer, in accordance with one embodiment.

FIG. 2 is a process flowchart that illustrates a method for making a non-blinking nanoparticle that comprises a core and a layered shell, wherein the shell can comprise at least one inner shell layer and at least one outer shell layer, in accordance with one embodiment. Therefore, in one aspect, provided herein is a method comprising: (Step 202) providing a mixture comprising a core and at least one coordinating solvent; (Step 204) adding a first inner shell precursor alternately with a second inner shell precursor in layer additions, to form an inner shell layer that is a desired number of layers thick; and (Step 206) adding a first outer shell precursor alternately with a second outer shell precursor in layer additions, to form an outer shell layer that is a desired number of layers thick. If the coordinating solvent of (Step 202) is not amine, the method further comprises an amine in (Step 202).

In some embodiments, the mixture can be heated to a temperature that is suitable for shell formation before and/or after every sequential addition of a shell precursor. In some embodiments, the shell is substantially uniform in coverage around the core and is substantially free of defects. In some embodiments, the nanoparticles have a diameter of less than about 15 nm In other embodiments, the nanoparticles have a diameter of between about 6 nm to about 10 nm The nanoparticles made by this method can have quantum yields greater than about 80%. The nanoparticle made by this method can have on-time fractions (i.e., ratio of the time that nanoparticle emission is turned "on" when the nanoparticle is excited) of greater than about 0.80 (under moderate to high excitation energy).

As discussed above, the overall size (diameter) of a donor/acceptor nanoparticle can significantly impact the theoretical limit of its FRET efficiency with a donor/acceptor moiety. Therefore, smaller nanoparticles are preferable for use in many FRET type applications. As such, FRET capable nanoparticles typically have diameters that are less than about 30 nm and preferably less than about 15 nm.

Moreover, many FRET type applications also require that the nanoparticles be water-dispersible or soluble in aqueous solutions. There are a number of suitable hydrophilic surface organic coatings (small organic ligands) that can be applied to the disclosed nanoparticles to make them soluble in aqueous solutions while still allowing them to be small enough to still be FRET capable. Some examples of small hydrophilic organic ligands that can be coated onto the disclosed nanoparticles, include but are not limited to, bidentate thiols (i.e., DHLA), tridentate thiols, dipeptides, functionalized organophosphorous compounds (e.g., phosphonic acids, phosphinic acids), etc.

Figure 3:
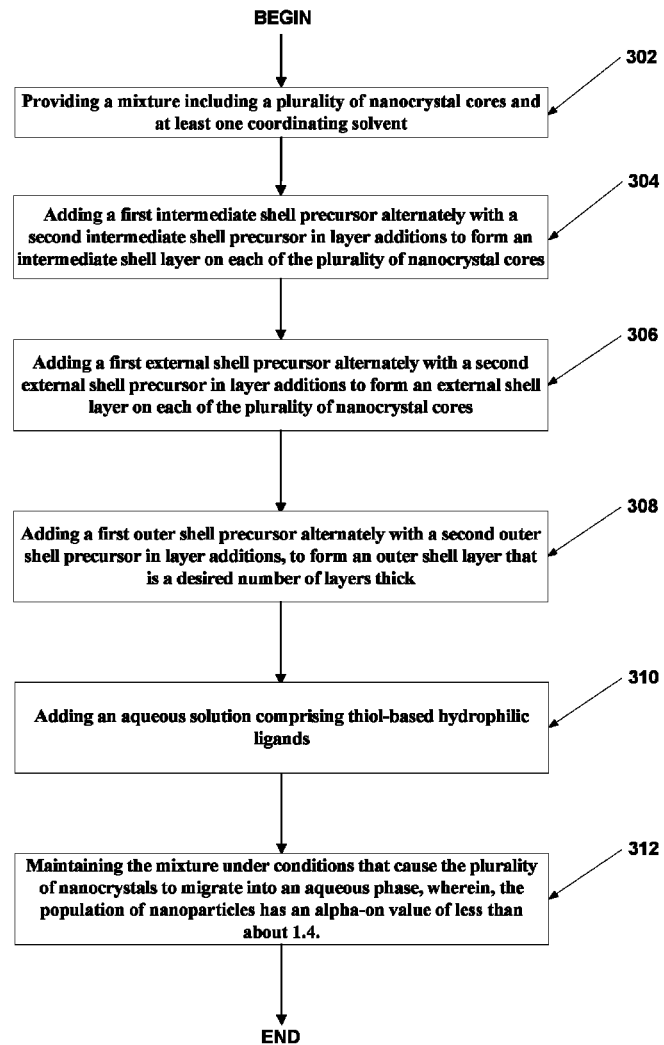
FIG. 3 is a process flowchart that illustrates a method for making a non-blinking nanoparticle or populations thereof that is comprised of a core and a layered shell, wherein the shell is comprised of at least one inner shell layer, at least one outer shell layer and a hydrophilic organic layer that is directly in contact with the outer shell layer, in accordance with one embodiment.

FIG. 3 is a process flowchart that illustrates a method for making a non-blinking nanoparticle or populations thereof that can comprise a core and a layered shell, wherein the shell is comprised of at least one inner shell layer, at least one outer shell layer and a hydrophilic organic layer that is directly in contact with the outer shell layer, in accordance with one embodiment. Thus, in another aspect, provided herein are methods for making a population of FRET capable nanoparticles that are non-blinking, comprising: (Step 302) providing a mixture including a plurality of nanocrystal cores and at least one coordinating solvent; (Step 304) adding a first intermediate shell precursor alternately with a second intermediate shell precursor in layer additions to form an intermediate shell layer on each of the plurality of nanocrystal cores; (Step 306) adding a first external shell precursor alternately with a second external shell precursor in layer additions to form an external shell layer on each of the plurality of nanocrystal cores; (Step 308) adding an aqueous solution comprising a hydrophilic ligand; and (Step 310) maintaining the mixture under conditions that cause the plurality of nanocrystals to migrate into an aqueous phase. In some embodiments, the resulting population of FRET capable non-blinking nanoparticles has an $\alpha_{on}$ value that is less than about 1.4. In other embodiments, the resulting population of FRET capable non-blinking nanoparticles has an on-time fraction of least about 0.8 (under moderate to high excitation energy). In some embodiments, the resulting population of FRET capable non-blinking nanoparticles has diameters that are less than about 15 nm. In some embodiments, the resulting population of FRET capable non-blinking nanoparticles has a FRET efficiency of at least 20%. In some embodiments, the resulting population of FRET capable non-blinking nanoparticles has a quantum yield of at least about 40%.

In some embodiments, a one step or a two step ligand exchange process is utilized to replace the hydrophobic ligands on the nanoparticles with hydrophilic ligands to cause the plurality of nanocrystals to migrate into the aqueous phase. See PCT Application Serial No. PCT/US09/53018 and PCT/US09/59456 which are expressly incorporated herein by reference as if set forth in full.

In some embodiments, the nanocrystal coated with hydrophobic ligands is dissolved in a co-solvent that is not miscible with water under the conditions used. The dispersion of the nanocrystal can optionally be contacted with a phase transfer agent before the addition of the aqueous solution comprising the hydrophilic ligand. In some embodiments the resultant mixture can be monophasic. In other embodiments, the resultant mixture can be biphasic, especially where the aqueous and non-aqueous phases are immiscible under the conditions used. In some embodiments, a phase transfer agent and/or a cosolvent can be combined with either the aqueous or non-aqueous solutions prior to formation of the biphasic mixture. In other embodiments, a phase transfer agent and/or a cosolvent can be added after formation of the biphasic mixture. The nanocrystal will ordinarily remain in the non-aqueous phase unless at least some hydrophobic ligands on the nanocrystal surface desorb from the nanocrystal and are replaced by hydrophilic ligands, because the hydrophobic ligands initially on the nanocrystal surface are incompatible with dispersal in the aqueous phase.

In another aspect, provided herein are methods of making a FRET capable nanoparticle and populations thereof that are non-blinking, comprising: (a) providing a mixture comprising a plurality of nanocrystal cores and at least one coordinating solvent; (b) adding a first intermediate shell precursor alternately with a second intermediate shell precursor in layer additions to form an intermediate shell layer on each of the plurality of nanocrystal cores, wherein the intermediate shell layer is comprised of more than one monolayer; (c) adding a first external shell precursor alternately with a second external shell precursor in layer additions to form an external shell layer on each of the plurality of nanocrystal cores, wherein the external shell layer is disposed on top of the intermediate shell layer and is comprised of more than one monolayer; (d) adding an aqueous solution comprising a hydrophilic ligand; and (e) maintaining the mixture under conditions that cause the plurality of nanocrystals to migrate into an aqueous phase. If the coordinating solvent is not an amine, at least one amine can be included in step (a). In some embodiments, the resulting population of FRET capable non-blinking nanoparticles has a $\alpha_{on}$ value that is less than about 1.4. In other embodiments, the resulting population of FRET capable non-blinking nanoparticles has an on-time fraction of least about 0.8 (under moderate to high excitation energy). In some embodiments, the resulting population of FRET capable non-blinking nanoparticles has diameters that are less than about 15 nm. In some embodiments, the resulting population of FRET capable non-blinking nanoparticles has a FRET efficiency of at least 20%. In some embodiments, the resulting population of FRET capable non-blinking nanoparticles has a quantum yield of at least about 40%.

In some embodiments, a one step or a two step ligand exchange process is utilized to replace the hydrophobic ligands on the nanoparticles with hydrophilic ligands to cause the plurality of nanocrystals to migrate into the aqueous phase. See PCT Application Serial No. PCT/US09/59409; PCT/US09/53018; and PCT/US09/59456 which are expressly incorporated herein by reference as if set forth in full.

Figure 4:
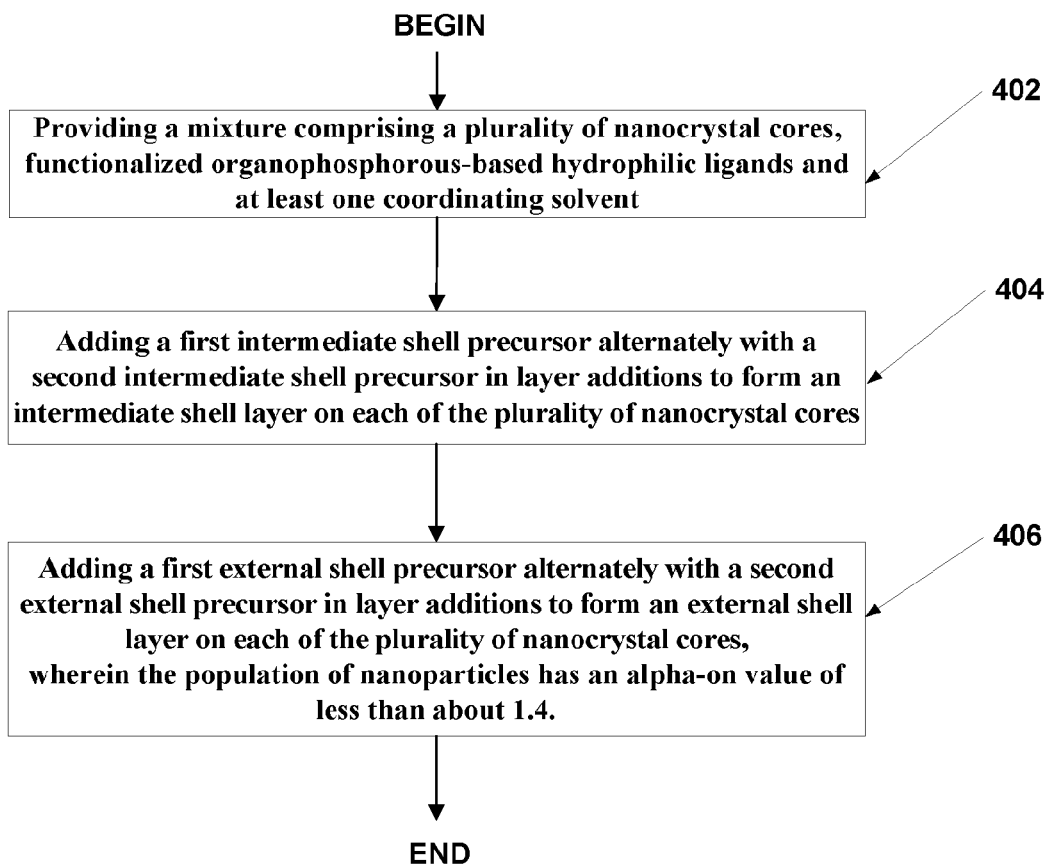
FIG. 4 is a process flowchart that illustrates a method for making a non-blinking nanoparticle or populations thereof that is comprised of a core and a layered shell, wherein the shell is comprised of at least one inner shell layer, at least one outer shell layer and a hydrophilic organic layer that is directly in contact with the outer shell layer, in accordance with one embodiment.
Figure 5:
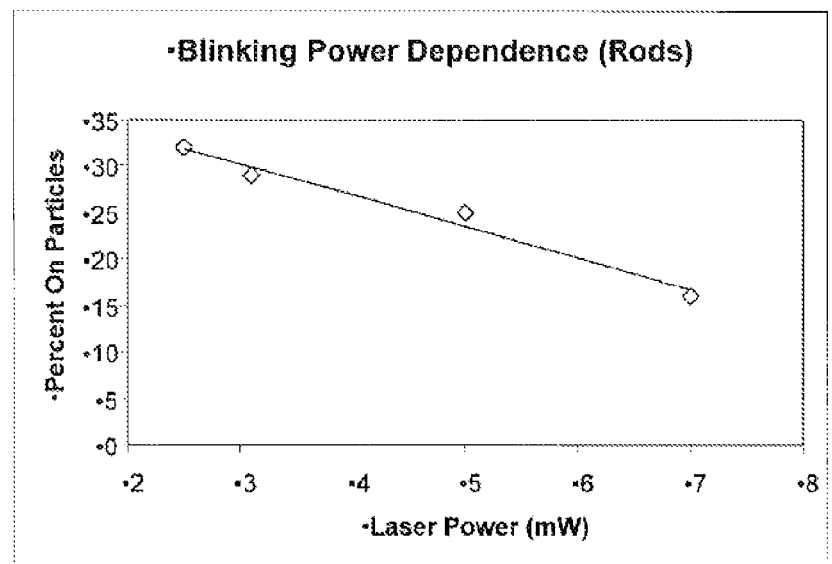
FIG. 5 shows blinking statistics of quantum dot 605 rods at various laser powers.
Figure 6:
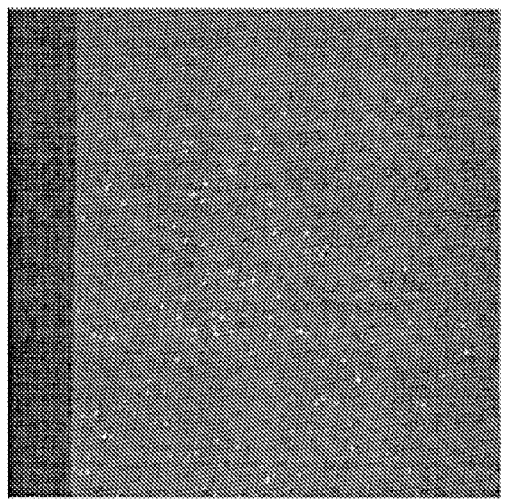
FIG. 6 (a) shows the blinking characteristics of quantum dot 605 rods; (b) shows the blinking characteristics of quantum dot 605 spheres.
Figure 6:
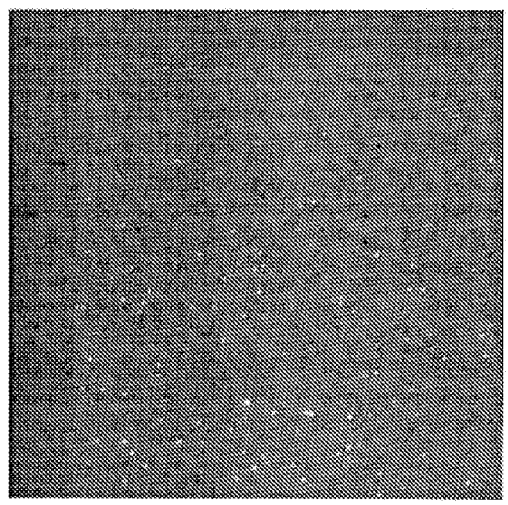

FIG. 4 is a process flowchart that illustrates a method for making a non-blinking nanoparticle or populations thereof that is comprised of a core and a layered shell, wherein the shell is comprised of at least one inner shell layer, at least one outer shell layer and a hydrophilic organic layer that is directly in contact with the outer shell layer, in accordance with one embodiment. Therefore, in another aspect, provided herein are methods of making a FRET capable nanoparticle and populations thereof that are non-blinking, comprising: (Step 402) providing a mixture comprising a plurality of nanocrystal cores, functionalized organophosphorous-based hydrophilic ligands and at least one coordinating solvent; (Step 404) adding a first intermediate shell precursor alternately with a second intermediate shell precursor in layer additions to form an intermediate shell layer on each of the plurality of nanocrystal cores; and (Step 406) adding a first external shell precursor alternately with a second external shell precursor in layer additions to form an external shell layer on each of the plurality of nanocrystal cores. In some embodiments, the resulting population of FRET capable non-blinking nanoparticles has an $\alpha_{on}$ value that is less than about 1.4. In other embodiments, the resulting population of FRET capable non-blinking nanoparticles has an on-time fraction of least about 0.8. In some embodiments, the resulting population of FRET capable non-blinking nanoparticles has diameters that are less than about 15 nm. In some embodiments, the resulting population of FRET capable non-blinking nanoparticles has a FRET efficiency of at least 20%. In some embodiments, the resulting population of FRET capable non-blinking nanoparticles has a quantum yield of at least about 40%.

In some embodiments, the functionalized organophosphorous-based hydrophilic ligands are multi-functional surface ligands that include a phosphonate/phosphinate nanocrystal binding center, a linker, and a functional group, which imparts functionality on the nanocrystal. As used herein the term "functional group" may refer to a group that affects reactivity, solubility, or both reactivity and solubility when present on a multi-functional surface ligand. Embodiments can include a wide variety of functional groups that can impart various types of functionality on the nanocrystal including hydrophilicity, water-solubility, or dispersability and/or reactivity, and the functionality may generally not include only hydrophobicity or only solubility in organic solvents without increasing reactivity. For example, a functional group that is generally hydrophobic but that increases reactivity such as an alkene or alkyne and certain esters and ethers can be encompassed by embodiments, whereas alkyl groups, which do not generally impart reactivity but increase hydrophobicity may be excluded.

In certain embodiments, the FRET capable and non-blinking nanoparticles produced by the disclosed methods may be coated with ligands that impart water solubility and/or reactivity on the nanoparticle obviating the need for ligand replacement. Without wishing to be bound by theory, eliminating ligand replacement may provide more consistent thermodynamic properties, which may lead to reduction in variability of coating and less loss of quantum yield, among other improvements in the properties of nanoparticles produced by the methods embodied herein. Eliminating ligand replacement may also allow for the production of nanoparticles having a wide variety of functional groups associated with the coating. In particular, while ligand replacement is generally limited to production of nanoparticles having amine and/or carboxylic acid functional groups, in various embodiments, the skilled artisan may choose among numerous functional groups when preparing the multi-functional ligands and may, therefore, generate nanoparticles that provide improved water-solubility or water-dispersity and/or support improved crosslinking and/or improved reactivity with cargo molecules. See PCT Application Serial No. PCT/US09/59117 which is expressly incorporated herein by reference as if set forth in full.

In another aspect, provided herein is a method of making a nanoparticle comprising a core and a layered gradient shell, wherein the shell comprises an multi-component (e.g., alloy, etc.) shell material of the form $M^1_xM^2_yX$, where x and y represent the ratio of $M^1$ and $M^2$ in the shell material, said method comprising: (a) providing a mixture comprising a core, at least one coordinating solvent; (b) heating said mixture to a temperature suitable for formation of the shell layer; and (c) adding a first inner shell precursor comprising $M^1_x$ and $M^2_y$ alternately with a second inner shell precursor comprising X in layer additions, wherein the ratio of y to x gradually increases in sequential layer additions, such that the shell layers becomes successively enriched in $M^2$, to form a layered gradient shell that is a desired number of monolayers thick. If the coordinating solvent is not an amine, at least one amine can be included in step (a).

In another embodiment, the methods described herein provide a nanoparticle having a layered gradient shell, wherein the core comprises CdSe and the shell comprises sequential layers of $Cd_xZn_yS$, where the ratio of y to x increases gradually from the innermost shell layer to the outermost shell layer, to provide a layered gradient shell with a finely graded potential. In some such embodiments, the outermost shell layer is essentially pure ZnS. In some embodiments, the percent of Zn in the gradient shell varies from less than about 10% at the innermost shell layer to greater than about 80% at the outermost shell layer.

Typically, the heating steps in the disclosed methods are conducted at a temperature within the range of about 150-350° C., more preferably within the range of about 200-300° C. In some embodiments, the temperature suitable for formation of at least one inner shell layer is about 215° C. In some embodiments, the temperature suitable for formation of at least one outer shell layer is about 245° C. It is understood that the above ranges are merely exemplary and are not intended to be limiting in any manner as the actual temperature ranges may vary, dependent upon the relative stability of the precursors, ligands, and solvents. Higher or lower temperatures may be appropriate for a particular reaction. The determination of suitable time and temperature conditions for providing nanoparticles is within the level of skill in the art using routine experimentation.

It can be advantageous to conduct the nanoparticle-forming reactions described herein with the exclusion of oxygen and moisture. In some embodiments the reactions are conducted in an inert atmosphere, such as in a dry box. The solvents and reagents are also typically rigorously purified to remove moisture and oxygen and other impurities, and are generally handled and transferred using methods and apparatus designed to minimize exposure to moisture and/or oxygen. In addition, the mixing and heating steps can be conducted in a vessel that is evacuated and filled and/or flushed with an inert gas such as nitrogen. The filling can be periodic or the filling can occur, followed by continuous flushing for a set period of time.

In some embodiments, the at least one coordinating solvent comprises a trialkylphosphine, a trialkylphosphine oxide, a phosphonic acid, or a mixture of these. Sometimes, the at least one coordinating solvent comprises TOP, TOPO, TDPA, OPA or a mixture of these. The solvent for these reactions often comprises a primary or secondary amine, for example, decylamine, hexadecylamine, or dioctylamine. In some embodiments, the amine is decylamine. In some embodiments, the first inner shell precursor is $Cd(OAc)_2$ and the second inner shell precursor is bis(trimethylsilyl)sulfide ($TMS_2S$). Sometimes, the first and second inner shell precursors are added as a solution in TOP. In some embodiments, the first outer shell precursor is $Et_2Zn$ and the second inner shell precursor is $TMS_2S$. Sometimes, the first and second outer shell precursors are added as a solution in TOP.

In certain embodiments, the disclosed nanoparticles may be prepared using the method described herein to build a layered CdS—ZnS shell on a CdSe quantum size core. The shells for these materials can have varying numbers of layers of CdS and ZnS. Prototypical materials containing a CdSe core and approximately 4 monolayers CdS and 3.5 monolayers of ZnS (the final 0.5 monolayer is essentially pure Zn), or a CdSe core and 9 monolayers CdS and 3.5 monolayers of ZnS were prepared as described in the examples.

In some embodiments, for either the inner or outer layer, or both, less than a full layer of the appropriate first shell precursor can be added alternately with less than a full layer of the appropriate second shell precursor, so the total amount of the first and second shell precursor required is added in two or more portions. Sometimes, the portion is about 0.25 monolayers of shell material, so that the 4 portions of 0.25 monolayer of first shell precursor are added alternately with 4 portions of 0.25 monolayer of second shell precursor; sometimes the portion is about 0.5 monolayers of shell material, and sometimes about 0.75 monolayers of shell material.

In another aspect, provided herein are methods of making a nanoparticle comprising a core and a layered gradient shell comprising an alloyed multi-component shell material of the form $M^1_xM^2_yX$, where $M^1$ and $M^2$ can be metal atoms and X can be a non metal atom, where x and y represent the ratio of $M^1$ and $M^2$ in the shell material, said method comprising: (a) providing a mixture comprising a core, at least one coordinating solvent and an amine; (b) heating said mixture to a temperature suitable for formation of the shell layer; (c) adding a first inner shell precursor comprising $M^1_x$ and $M^2_y$ alternately with a second inner shell precursor comprising X in layer additions, wherein the ratio of y to x gradually increases in sequential layer additions, such that the shell layers becomes successively enriched in $M^2$, to form a layered gradient shell that is a desired number of monolayers thick.

The size and uniformity of nanoparticles can be achieved by sequentially applying monolayers of shell material to the core. Typically, the shell monolayers are of relatively uniform size or depth. The monolayer additions require the addition of an appropriate amount of the shell precursors to form a single monolayer, based on the starting size of the underlying core. This means that as each monolayer of shell material is added, a new "core" size can be determined by taking the previous "core" size and adding to it the thickness of just-added shell monolayer. This leads to a slightly larger volume of the following shell material needing to be added for each subsequent monolayer of shell material being added.

Some embodiments of the nanoparticles prepared by the methods disclosed herein demonstrate modulated or suppressed blinking relative to classically blinking nanoparticles of similar composition(s). In some embodiments, the methods described herein are used to provide nanoparticles having a layered shell of about 3-20 monolayers, sometimes from about 5-14 monolayers, sometimes from about 6-12 monolayers, sometimes from about 7-10 monolayers. In certain embodiments, the methods provide nanoparticles having an on-time fraction of greater than about 0.80, preferably greater than about 0.95 (under moderate to high excitation energy).

The nanocrystal core and shell can be made of any suitable metal and non-metal atoms that are known to form semiconductor nanocrystals. Suitable semiconductor materials for the core and/or shell include, but are not limited to, ones including Group 2-16, 12-16, 13-15 and 14 element-based semiconductors such as ZnS, ZnSe, ZnTe, CdS, CdSe, CdTe, HgS, HgSe, HgTe, MgS, MgSe, MgTe, CaS, CaSe, CaTe, SrS, SrSe, SrTe, BaS, BaSe, BaTe, GaN, GaP, GaAs, GaSb, InP, InAs, InSb, AlAs, AlP, AlSb, PbS, PbSe, Ge and Si and ternary and quaternary mixtures thereof. In some embodiments, the core and the shell of a core/shell nanocrystal are composed of different semiconductor materials, meaning that at least one atom type of a binary semiconductor material of the core of a core/shell is different from the atom types in the shell of the core/shell nanocrystal.

Nanoparticles prepared by the methods described herein comprise a layered shell that is substantially uniform in coverage around the core and is substantially free of defects. In frequent embodiments, the nanoparticles provided by the methods described herein are spherical or spheroidal. In preferred embodiments, the nanoparticles provided by the methods described herein have a quantum yield of greater than about 40%, preferably greater than about 50%, more preferably greater than about 60%, greater than about 70%, or greater than about 80%.

Suitable materials for the shell include semiconductor materials having a higher bandgap energy than the semiconductor nanocrystal core. In addition to having a bandgap energy greater than the semiconductor nanocrystal core, suitable materials for the shell can in certain embodiments have good conduction and valence band offset with respect to the core semiconductor nanocrystal. Thus, the conduction band is desirably higher and the valence band is desirably lower than those of the core semiconductor nanocrystal. For semiconductor nanocrystal cores that emit energy in the visible (e.g., CdS, CdSe, CdTe, ZnS, ZnSe, ZnTe, GaP, GaAs, GaN)

or near IR (e.g., InP, InAs, InSb, PbS, PbSe), a material that has a bandgap energy in the ultraviolet regions may be used. Exemplary materials include CdS, CdSe, InP, InAs, ZnS, ZnSe, ZnTe, GaP, GaN, and magnesium chalcogenides, e.g., MgS, MgSe, and MgTe. For a semiconductor nanocrystal core that emits in the near IR, materials having a bandgap energy in the visible, such as CdS or CdSe, may also be used. The preparation of a coated semiconductor nanocrystal may be found in, e.g., Dabbousi et al. (1997) *J. Phys. Chem. B* 101:9463, Hines et al. (1996) *J. Phys. Chem.* 100: 468-471, Peng et al. (1997) *J. Am. Chem. Soc.* 119:7019-7029, and Kuno et al. (1997) *J. Phys. Chem.* 106:9869. It is also understood in the art that the actual fluorescence wavelength for a particular nanocrystal core depends upon the size of the core as well as its composition, so the categorizations above are approximations, and nanocrystal cores described as emitting in the visible or the near IR can actually emit at longer or shorter wavelengths depending upon the size of the core.

In some embodiments, the metal atoms of a shell layer are selected from Cd, Zn, Ga and Mg. The second element in these semiconductor shell layers is frequently selected from S, Se, Te, P, As, N and Sb.

Precursors useful as the "first" precursor in the methods provided herein include compounds containing elements from Groups 2 and 12 of the Periodic Table of the Elements (e.g., Zn, Cd, Hg, Mg, Ca, Sr, Ba, and the like), compounds containing elements from Group 13 of the Periodic Table of the Elements (Al, Ga, In, and the like), and compounds containing elements from Group 14 of the Periodic Table of the Elements (Si, Ge, Pb, and the like). Many forms of the precursors can be used in the disclosed methods.

Examples of compounds useful as the first precursor can include, but are not limited to: organometallic compounds such as alkyl metal species, salts such as metal halides, metal acetates, metal carboxylates, metal phosphonates, metal phosphinates, metal oxides, or other salts. In some embodiments, the first precursor provides a neutral species in solution. For example, alkyl metal species such as diethylzinc ($Et_2Zn$) or dimethyl cadmium are typically considered to be a source of neutral zinc atoms ($Zn^0$) in solution. In other embodiments, the first precursor provides an ionic species (i.e., a metal cation) in solution. For example, zinc chloride ($ZnCl_2$) and other zinc halides, zinc acetate ($Zn(OAc)_2$) and zinc carboxylates are typically considered to be sources of $Zn^{2+}$ cations in solution.

By way of example only, suitable first precursors providing neutral metal species include dialkyl metal sources, such as dimethyl cadmium ($Me_2Cd$), diethyl zinc ($Et_2Zn$), and the like. Suitable first precursors providing metal cations in solution include, e.g., cadmium salts, such as cadmium acetate ($Cd(OAc)_2$), cadmium nitrate ($Cd(NO_3)_2$), cadmium oxide (CdO), and other cadmium salts; and zinc salts such as zinc chloride ($ZnCl_2$), zinc acetate ($Zn(OAc)_2$), zinc oleate ($Zn$ (oleate)$_2$), zinc chloro(oleate), zinc undecylenate, zinc salicylate, and other zinc salts. In some embodiments, the first precursor is salt of Cd or Zn. In some embodiments, it is a halide, acetate, carboxylate, or oxide salt of Cd or Zn. In other embodiments, the first precursor is a salt of the form $M(O_2CR)X$, wherein M is Cd or Zn; X is a halide or $O_2CR$; and R is a C4-C24 alkyl group that is optionally unsaturated. Other suitable forms of Groups 2, 12, 13 and 14 elements useful as first precursors are known in the art.

Precursors useful as the "second" precursor in the disclosed methods include compounds containing elements from Group 16 of the Periodic Table of the Elements (e.g., S, Se, Te, and the like), compounds containing elements from Group 15 of the Periodic Table of the Elements (N, P, As, Sb, and the like), and compounds containing elements from Group 14 of the Periodic Table of the Elements (Ge, Si, and the like). Many forms of the precursors can be used in the disclosed methods. It will be understood that in some embodiments, the second precursor will provide a neutral species in solution, while in other embodiments the second precursor will provide an ionic species in solution.

When the first precursor comprises a metal cation, the second precursor can provide an uncharged (i.e., neutral) non-metal atom in solution. In frequent embodiments, when the first precursor comprises a metal cation, the second precursor contributes a neutral chalcogen atom, most commonly $S^0$, $Se^0$ or $Te^0$.

Suitable second precursors for providing a neutral chalcogen atom include, for example, elemental sulfur (often as a solution in an amine, e.g., decylamine, oleylamine, or dioctylamine, or an alkene, such as octadecene), and tri-alkylphosphine adducts of S, Se and Te. Such trialkylphosphine adducts are sometimes described herein as $R3P=X$, wherein X is S, Se or Te, and each R is independently H, or a $C_1$-$C_{24}$ hydrocarbon group that can be straight-chain, branched, cyclic, or a combination of these, and which can be unsaturated. Exemplary second precursors of this type include tri-n (butylphosphine)selenide (TBP=Se), tri-n-(octylphosphine)selenide (TOP=Se), and the corresponding sulfur and tellurium reagents, TBP=S, TOP=S, TBP=Te and TOP=Te. These reagents are frequently formed by combining a desired element, such as Se, S, or Te with an appropriate coordinating solvent, e.g., TOP or TBP. Precursors that provide anionic species under the reaction conditions are typically used with a first precursor that provides a neutral metal atom, such as alkylmetal compounds and others described above or known in the art.

In some embodiments, the second precursor provides a negatively charged non-metal ion in solution (e.g., S-2, Se-2 or Te-2). Examples of suitable second precursors providing an ionic species include silyl compounds such as bis(trimethylsilyl)selenide (($TMS)_2Se$), bis(trimethylsilyl)sulfide (($TMS)_2S$) and bis(trimethylsilyl)telluride (($TMS)_2Te$). Also included are hydrogenated compounds such as H2Se, H2S, H2Te; and metal salts such as NaHSe, NaSH or NaHTe. In this situation, an oxidant can be used to oxidize a neutral metal species to a cationic species that can react with the anionic precursor in a 'matched' reaction, or an oxidant can be used increase the oxidation state of the anionic precursor to provide a neutral species that can undergo a 'matched' reaction with a neutral metal species.

Other exemplary organic precursors are described in U.S. Pat. Nos. 6,207,299 and 6,322,901 to Bawendi et al., and synthesis methods using weak acids as precursor materials are disclosed by Qu et al., (2001), Nano Lett., 1(6):333-337, the disclosures of each of which are incorporated herein by reference in their entirety.

Both the first and the second precursors can be combined with an appropriate solvent to form a solution for use in the disclosed methods. The solvent or solvent mixture used to form a first precursor solution may be the same or different from that used to form a second precursor solution. Typical coordinating solvents include alkyl phosphines, alkyl phosphine oxides, alkyl phosphonic acids, alkyl phosphinic acids, or carboxylic acid containing solvents, or mixtures of these.

Suitable reaction solvents include, by way of illustration and not limitation, hydrocarbons, amines, alkyl phosphines, alkyl phosphine oxides, carboxylic acids, ethers, furans, phosphoacids, pyridines and mixtures thereof. The solvent may actually comprise a mixture of solvents, often referred to in the art as a "solvent system". In some embodiments, the solvent comprises at least one coordinating solvent. In some embodiments, the solvent system comprises a secondary amine and a trialkyl phosphine (e.g., TBP or TOP) or a trialkylphosphine oxide (e.g., TOPO). If the coordinating solvent is not an amine, an amine can be included.

A coordinating solvent might be a mixture of an essentially non-coordinating solvent such as an alkane and a ligand as defined below.

Suitable hydrocarbons include alkanes, alkenes and aromatic hydrocarbons from 10 to about 30 carbon atoms; examples include octadecene and squalane. The hydrocarbon may comprise a mixture of alkane, alkene and aromatic moieties, such as alkylbenzenes (e.g., mesitylene).

Suitable amines include, but are not limited to, monoalkylamines, dialkylamines, and trialkylamines, for example dioctylamine, oleylamine, decylamine, dodecylamine, hexyldecylamine, and so forth. Alkyl groups for these amines typically contain about 6-24 carbon atoms per alkyl, and can include an unsaturated carbon-carbon bond, and each amine typically has a total number of carbon atoms in all of its alkyl groups combined of about 10-30 carbon atoms.

Exemplary alkyl phosphines include, but are not limited to, the trialkyl phosphines, tri-n-butylphosphine (TBP), tri-n-octylphosphine (TOP), and so forth. Alkyl groups for these phosphines contain about 6-24 carbon atoms per alkyl, and can contain an unsaturated carbon-carbon bond, and each phosphine has a total number of carbon atoms in all of its alkyl groups combined of about 10-30 carbon atoms.

Suitable alkyl phosphine oxides include, but are not limited to, the trialkyl phosphine oxide, tri-n-octylphosphine oxide (TOPO), and so forth. Alkyl groups for these phosphine oxides contain about 6-24 carbon atoms per alkyl, and can contain an unsaturated carbon-carbon bond, and each phosphine oxide has a total number of carbon atoms in all of its alkyl groups combined of about 10-30 carbon atoms.

Exemplary fatty acids include, but are not limited to, stearic, oleic, palmitic, myristic and lauric acids, as well as other carboxylic acids of the formula R—COOH, wherein R is a C6-C24 hydrocarbon group and can contain an unsaturated carbon-carbon bond. It will be appreciated that the rate of nanocrystal growth generally increases as the length of the fatty acid chain decreases.

Exemplary ethers and furans include, but are not limited to, tetrahydrofuran and its methylated forms, glymes, and so forth.

Suitable phosphonic and phosphinic acids include, but are not limited to hexylphosphonic acid (HPA), tetradecylphosphonic acid (TDPA), and octylphosphinic acid (OPA), and are frequently used in combination with an alkyl phosphine oxide such as TOPO. Suitable phosphonic and phosphinic acids are of the formula $RPO_3H_2$ or $R_2PO_2H$, wherein each R is independently a C6-C24 hydrocarbon group and can contain an unsaturated carbon-carbon bond.

Exemplary pyridines include, but are not limited to, pyridine, alkylated pyridines, nicotinic acid, and so forth.

Suitable alkenes include, e.g., octadecene and other C4-C24 hydrocarbons that are unsaturated.

Solvents can be used alone or in combination. TOP-TOPO solvent systems are commonly utilized in the art, as are other related (e.g., butyl) systems. For example, TOP and TOPO can be used in combination to form a cadmium solution, while TOP, alone, can be used to form a selenium solution. Also preferred are solvent mixtures comprising an amine, in particular a secondary amine, with a trialkylphosphine oxide, such as TOPO.

Technical grade solvents can be used, and benefits can be obtained from the existence of beneficial impurities in such solvents, e.g. TOP, TOPO or both. In certain embodiments, the solvent comprises at least one coordinating solvent. In one preferred embodiment, the solvent is pure. Typically, this means that the solvent contains less than about 10 vol %, and more preferably less than about 5 vol % of impurities that can function as reductants. Therefore, solvents such as TOPO at about 90% or about 97% purity and TOP at about 90% purity are particularly well suited for use in the disclosed methods, and solvents that are greater than about 99% pure are preferred.

In some embodiments, ligands are included in the reaction. Ligands are compounds that complex with a precursor and/or a nanoparticle. Suitable ligands include, by way of illustration and not limitation, phospho-acids such as hexylphosphonic acid and tetradecylphosphonic acid (TDPA), carboxylic acids such as isomers of octadecanoic acid, amines, amides, alcohols, ethers, alkenes, and alkynes. In some cases, the ligand and the solvent can be the same.

Nanoparticle core or shell precursors can be represented as a M-source and an X-donor. The M-source can be an M-containing salt, such as a halide, carboxylate, phosphonate, carbonate, hydroxide, or diketonate, or a mixed salt thereof (e.g., a halo carboxylate salt, such as Cd(halo)(oleate)), of a metal, M, in which M can be, e.g., Cd, Zn, Mg, Hg, Al, Ga, In, or Tl. In the X-donor, X can be, e.g., O, S, Se, Te, N, P, As, or Sb. The mixture can include an amine, such as a primary amine (e.g., a C8-C20 alkyl amine). The X donor can include, for example, a phosphine chalcogenide, a bis(trialkylsilyl)chalcogenide, a dioxygen species, an ammonium salt, or a tris(trialkylsilyl)phosphine, or the like.

The M-source and the X donor can be combined by contacting a metal, M, or an M-containing salt, and a reducing agent to form an M-containing precursor. The reducing agent can include an alkyl phosphine, a 1,2-diol or an aldehyde, such as a $C_6$-$C_{20}$ alkyl diol or a $C_6$-$C_{20}$ aldehyde.

Suitable M-containing salts include, for example, cadmium acetylacetonate, cadmium iodide, cadmium bromide, cadmium chloride, cadmium hydroxide, cadmium carbonate, cadmium acetate, cadmium oxide, zinc acetylacetonate, zinc iodide, zinc bromide, zinc chloride, zinc hydroxide, zinc carbonate, zinc acetate, zinc oxide, magnesium acetylacetonate, magnesium iodide, magnesium bromide, magnesium chloride, magnesium hydroxide, magnesium carbonate, magnesium acetate, magnesium oxide, mercury acetylacetonate, mercury iodide, mercury bromide, mercury chloride, mercury hydroxide, mercury carbonate, mercury acetate, aluminum acetylacetonate, aluminum iodide, aluminum bromide, aluminum chloride, aluminum hydroxide, aluminum carbonate, aluminum acetate, gallium acetylacetonate, gallium iodide, gallium bromide, gallium chloride, gallium hydroxide, gallium carbonate, gallium acetate, indium acetylacetonate, indium iodide, indium bromide, indium chloride, indium hydroxide, indium carbonate, indium acetate, thallium acetylacetonate, thallium iodide, thallium bromide, thallium chloride, thallium hydroxide, thallium carbonate, or thallium acetate. Suitable M-containing salts also include, for example, carboxylate salts, such as oleate, stearate, myristate, and palmitate salts, mixed halo carboxylate salts, such as M(halo)(oleate) salts, as well as phosphonate salts.

Alkyl is a branched or unbranched saturated hydrocarbon group of 1 to 100 carbon atoms, preferably 1 to 30 carbon atoms, such as methyl, ethyl, n-propyl, isopropyl, n-butyl, isobutyl, t-butyl, octyl, decyl, tetradecyl, hexadecyl, eicosyl, tetracosyl and the like, as well as cycloalkyl groups such as cyclopentyl, cyclohexyl and the like. Optionally, an alkyl can contain 1 to 6 linkages selected from the group consisting of —O—, —S—, -M- and —NR— where R is hydrogen, or C1-C8 alkyl or lower alkenyl.

The X donor is a compound capable of reacting with the M-containing salt to form a material with the general formula MX. The X donor is generally a chalcogenide donor or a phosphine donor, such as a phosphine chalcogenide, a bis (silyl) chalcogenide, dioxygen, an ammonium salt, or a tris (trialkylsilyl) phosphine. Suitable X donors include dioxygen, elemental sulfur, bis(trimethylsilyl) selenide ((TMS)$_2$Se), trialkyl phosphine selenides such as (tri-n-octylphosphine) selenide (TOPSe) or (tri-n-butylphosphine) selenide (TBPSe), trialkyl phosphine tellurides such as (tri-n-octylphosphine) telluride (TOPTe) or hexapropylphosphorustriamide telluride (HPPTe), bis(trimethylsilyl)telluride ((TMS)$_2$Te), sulfur, bis(trimethylsilyl)sulfide ((TMS)$_2$S), a trialkyl phosphine sulfide such as (tri-n-octylphosphine) sulfide (TOPS), tris(dimethylamino) arsine, an ammonium salt such as an ammonium halide (e.g., NH$_4$Cl), tris(trimethylsilyl) phosphide ((TMS)$_3$P), tris(trimethylsilyl) arsenide ((TMS)$_3$As), or tris(trimethylsilyl) antimonide ((TMS)$_3$Sb). In certain embodiments, the M donor and the X donor can be moieties within the same molecule.

In some embodiments, mismatched precursors can be chosen such that one precursor provides a neutral atom in solution under the reaction conditions, while the other precursor provides an ion. For example, a mixture of cadmium alkylphosphonate, which is a source of Cd$^{2+}$ ions, and trioctylphosphine selenide (TOPSe), which is a source of Se$^0$, might be employed as mismatched precursors. Such precursors cannot react to form a neutral species unless an electron transfer agent is present to adjust the oxidation state of one of the reactive species to provide 'matched' species capable of undergoing reaction. For example, a reductant could be used to add electrons to Cd$^{2+}$ to provide two non-ionic species (i.e., Cd$^0$ and Se$^0$), or it could add electrons to Se$^0$ to provide two ionic species (i.e., Cd$^{2+}$ and Se$^{2-}$). Either way, once the atomic species are 'matched', their reaction can proceed, but the reaction cannot proceed without such an electron transfer agent. Alternatively, two ionic species having the same charge (i.e., two cations or two anions) would also be considered to be 'mismatched.' For example, mismatched precursors that provide two cationic species could be used, where one species is reduced to provide an anionic species capable of undergoing a 'matched' reaction. For example, Se$^{2+}$ or Se$^{4+}$ could be reduced to provide selenide anion Se$^{2-}$, which could undergo reaction with a metal cation species, such as Cd$^{2+}$. In another example, two cationic species could both be reduced to neutral species.

Applications for Non-blinking Nanoparticles

The nanoparticles provided herein can be used in a variety of single molecule microscopy and high throughput applications. Such application include but are not limited to single-molecule FRET measurements with flexibly linked dyes to derive full 3D structures of DNA constructs (see, e.g., Wozniak et al., Proc. Natl. Acad. Sci. U.S.A. 25; 105(47): 18337-42 (2008)); fluorescence correlation spectroscopy; real-time single molecule interactions such as RNA/DNA or protein-ligand; real-time single molecule DNA sequencing; analyte detection in tissues, fluid samples, cells, electrophoresis and other separation systems; intracellular and extracellular protein trafficking and localization; enzyme kinetics and control; protein sequencing; single molecule PCR (see, e.g., Kratysberg, et al., Methods 46(4):269-73 (2008)); as well as macromolecular structural analysis (see, e.g., Muschielok, et. al., Nat. Methods 5(11):965-71 (2008)).

In some embodiments, a nanoparticle may be conjugated to a molecule or species for detection by means of FRET. In some embodiments, the FRET efficiency in a FRET reaction of the disclosed nanoparticles can be at least about 25%, at least about 40%, at least about 50%, at least about 60%, at least about 70%, at least about 80%, at least about 90%, or greater up to 100%.

Examples of conjugates include, but are not limited to, dipeptide, dipeptide-BSA, dipeptide-BSA-biotin, dipeptide-BSA-streptavidin, dipeptide-BSA-biotin-polymerase, and dipeptide-BSA-HIS-polymerase conjugates. In a specific embodiment, the conjugate comprises Klenow (1×, 5×, & 15× polymerases per nanoparticle). In another specific embodiment, the conjugate can comprise phi-29 (1×, 5×, and 15× polymerases per nanoparticle). For example, nanoparticles coated with DHLA can be conjugated to a His6-modified polymerase, with optional inclusion of coating proteins such as BSA or inert His6-modified proteins.

The following examples are offered to illustrate but not to limit the embodiments described herein.

EXAMPLE 1

Preparation of Core-Shell Nanoparticle
CdSe/4CdS-3.5ZnS

Core Synthesis:

Cores are prepared using standard methods, such as those described in U.S. Pat. No. 6,815,064, the only change being that the growth is halted at 535 nm emission. These cores were precipitated and cleaned in the standard methods and resuspended into hexane for use in the shell reaction.

Shell Synthesis:

A 1:1 (w:v) mixture of tri-n-octylphosphine oxide (TOPO) and tri-n-octylphosphine (TOP) was introduced into a flask. Tetradecylphosphonic acid (TDPA) was added to the flask in an amount suitable to fully passivate the final material, as can be calculated from the reaction scale and the expected final nanoparticle size. The contents of the flask were heated to 125° C. under vacuum and then the flask was refilled with N$_2$ and cooled.

Inside the glovebox, a solution of a suitable cadmium precursor (such as dimethylcadmium or cadmium acetate) in TOP was prepared in a quantity sufficient to produce a desired thickness of shell, as can be calculated by one of ordinary skill in the art. When a zinc shell was also desired, a solution of a suitable zinc precursor (such as diethylzinc or zinc stearate) was prepared in TOP in a quantity sufficient to produce the desired shell thickness. Separately, a solution of trimethylsilylsulfide [(TMS)$_2$S] in TOP was prepared in a quantity sufficient to produce the desired shell thickness. Each of these solutions was taken up in separate syringes and removed from the glove box.

Of the previously prepared core/hexane solution, 17 mL (at an optical density of 21.5 at the band edge) was added to the reaction flask and the hexane was removed by vacuum; the flask was then refilled with N$_2$. The flask was heated to the desired synthesis temperature, typically about 200 to about 250° C. During this heat-up, 17 mL of decylamine was added.

The cadmium and sulfur precursor solutions were then added alternately in layer additions, which were based upon the starting size of the underlying cores. So this means that as each layer of shell material was added, a new "core" size was determined by taking the previous "core" size and adding to it the thickness of just-added shell material. This leads to a slightly larger volume of the following shell material needing to be added for each subsequent layer of shell material.

After a desired thickness of CdS shell material was added, the cadmium precursor solution was replaced with the zinc precursor solution. Zinc and sulfur solutions were then added alternately in layer additions until a desired thickness of ZnS was added. A final layer of the zinc solution was added at the end, the reaction flask was cooled, and the product was isolated by conventional precipitation methods.

EXAMPLE 2

Comparison of Blinking Properties

The blinking behavior of CdSe/CdS/ZnS nanoparticles prepared as in Example 1 were evaluated using a standard single-particle microscopy (TIRF) set up, under conditions of continuous irradiation with 405 nm laser with a desired input power. The particles described here were prepared with a CdS shell approximately 4 monolayers thick and a ZnS shell approximately 3 monolayers thick, and were compared to commercially available nanoparticles prepared by conventional methods.

As discussed above, more blinking has generally been observed with increasing laser power. In addition, the particles blink on a larger number of timescales and may spend a larger percent of time in the off state at higher laser power. To explore the effect of laser power on blinking, nanoparticles were irradiated using a high intensity blue-violet laser, having an excitation wavelength of about 405 nm. The laser was tuned to control the power, and the laser power was measured before it reached the lens. Less blinking would be expected for photo-excitation using a laser having a longer wavelength as a result of the smaller absorption cross-section of the particles at longer wavelengths. In particular, for very large nanoparticles having very thick shells, more blinking would be expected at shorter wavelengths owing to the greater amount of absorbance by the shell materials at wavelengths in the blue-violet or ultraviolet range. In addition, very large nanoparticles having very thick shells would be expected to show a greater amount of photo-bleaching at decreased wavelength, due to an increase in photoexcitation at shorter wavelengths.

For comparative purposes, blinking statistics were determined at various laser powers for both the commercially available nanoparticles prepared via conventional methods and the new nanoparticles disclosed herein prepared using the standard successive ion addition methods to produce a 4 monolayer CdS layer and a 3.5 monolayer ZnS layer. Because the nanoparticles disclosed herein show markedly reduced blinking, conventional analysis via fitting the distribution of "on" durations and "off" durations to a power law was found to be limited. The relatively infrequent blinking of the new nanoparticles meant that a typical 20 minute movie would often not capture enough blinks to support fitting of any kind.

This fitting failure resulting from having too few blinks in a 20 minute movie was used as a mode of analysis of the blinking. It was found that at an excitation rate of 420,000 absorbed photons per second, only 26% of the conventional nanoparticles showed this low-blinking behavior, and when the excitation rate was increased to 690,000 absorbed photons per second, this number dropped to 16%. In contrast, even at excitation rates of 970,000 absorbed photons per second, fully 76% of the nanoparticles disclosed herein showed this low-blinking behavior, and that number dropped only to 65% when the excitation rate was increased to 1,600,000 absorbed photons per second. Note that for both samples, blinking was exacerbated by higher excitation rates, as is commonly described in the field. Thus, the observation that far more of the new particles showed low-blinking behavior, even at higher excitation rates, is significant.

In addition, a more conventional analysis using the power law parameters for those particles that could be fit to a power law also showed a marked difference between the samples. The particles were binned into three categories: low-blinkers for which no power law fit could be obtained as a result of too little blinking (which typically indicated an $\alpha_{on}$ of below about 1.1), mid-blinkers for which an $\alpha_{on}$ of below 1.4 was measured, and high-blinkers for which an $\alpha_{on}$ of above 1.4 was measured. For the conventional particles, under an excitation rate of 170,000 photons per second, the distribution of low-medium-high blinking under these criteria was 33%-40%-27%. For the nanoparticles disclosed herein, under an increased excitation rate of 390,000 absorbed photons per second, the low-medium-high distribution was 81%-8%-11%. Given the clear decrease in blinking, even at higher excitation rates, it is apparent that the particles disclosed herein are markedly beneficial.

What is claimed is:
1. A population of nanoparticles, comprising:
a plurality of core/shell nanocrystals, each including,
a semiconductor core;
an intermediate semiconductor shell layer comprising more than one monolayer disposed over the semiconductor core;
an external semiconductor shell layer disposed over the intermediate semiconductor shell layer; and
a hydrophilic organic layer in direct contact with the external semiconductor shell layer, wherein the hydrophilic organic layer comprises a plurality of hydrophilic ligands, each comprising a hydrophilic functional group that imparts aqueous dispersibility to the nanocrystal, wherein the hydrophilic ligands are selected from dipeptides, tridentate thiol ligands, and functionalized phosphonate or phosphinate ligands, wherein the tridentate thiol ligands are selected from the group consisting of compounds of Formula I, II, III, IV, V, and VI:

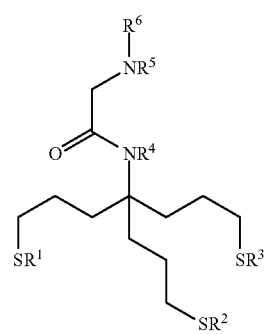

I

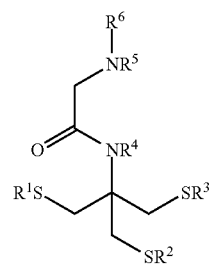

II

-continued

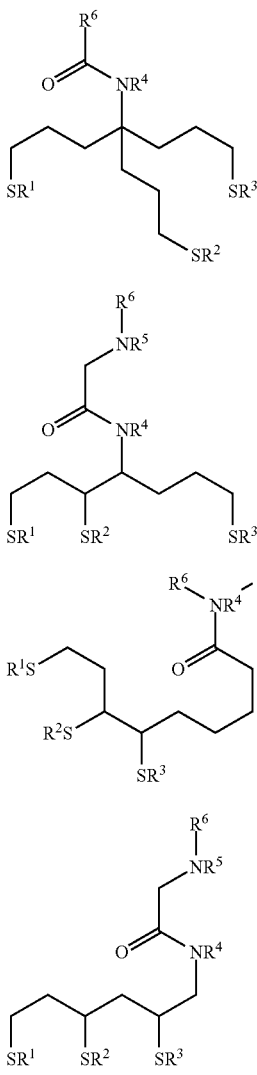

wherein $R^1$, $R^2$, and $R^3$, when taken alone, are independently H, halo, hydroxyl, (—(C═O)—$C_1$-$C_{22}$ or —(C═O)$CF_3$) alkanoyl, $C_1$-$C_{22}$ alkyl, $C_1$-$C_{22}$ heteroalkyl, ((CO)O$C_1$-$C_{22}$) alkylcarbonato, or —(CO)NH($C_1$-$C_{20}$) or —(CO)N($C_1$-$C_{20}$)$_2$) alkylcarbamoyl;

$R^4$, and $R^5$, when taken alone, are independently H, $C_1$-$C_{20}$ alkyl, or $C_6$-$C_{18}$ aryl; and $R^6$ is H or a polyethylene glycol moiety.

2. The population of nanoparticles, as recited in claim 1, wherein the population of nanoparticles further comprises donor moieties or acceptor moieties, wherein the nanoparticles undergo FRET with the donor moieties or acceptor moieties.

3. The population of nanoparticles, as recited in claim 2, wherein the population of nanoparticles has a FRET efficiency of greater than 20%.

4. The population of nanoparticles, as recited in claim 1, wherein the hydrophilic ligand is a tridentate thiol.

5. The population of nanoparticles, as recited in claim 1, wherein the hydrophilic ligand is a dipeptide.

6. The population of nanoparticles, as recited in claim 1, wherein the hydrophilic ligand is a functionalized phosphonate.

7. The population of nanoparticles, as recited in claim 1, wherein the hydrophilic ligand is a functionalized phosphinate.

8. The population of nanoparticles, as recited in claim 1, wherein greater than 75% of the population of nanoparticles have diameters of less than about 15 nm.

9. The population of nanoparticles, as recited in claim 1, wherein the external semiconductor shell layer is comprised of more than one monolayer.

10. A method for producing a population of nanoparticles, comprising:

providing a mixture including a plurality of nanocrystal cores and at least one coordinating solvent;

adding a first intermediate shell precursor alternately with a second intermediate shell precursor in layer additions to form an intermediate shell layer comprising more than one monolayer on each of the plurality of nanocrystal cores;

adding a first external shell precursor alternately with a second external shell precursor in layer additions to form an external shell layer on each of the plurality of nanocrystal cores;

adding an aqueous solution comprising hydrophilic ligands, wherein each hydrophilic ligand comprises a hydrophilic functional group that imparts aqueous dispersibility to the nanocrystal, wherein the hydrophilic ligands are selected from dipeptides, tridentate thiol ligands, and functionalized phosphonate or phosphinate ligands, wherein the tridentate thiol ligands are selected from the group consisting of compounds of Formula I, II, III, IV, V, or VI:

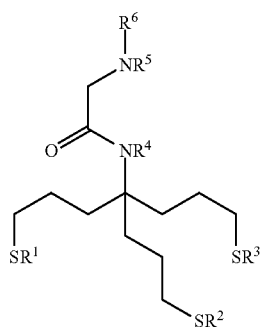

I

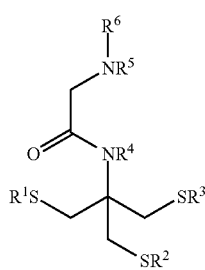

II

-continued

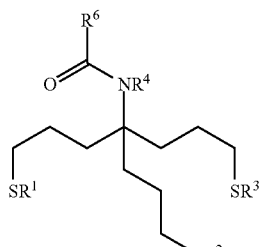
III

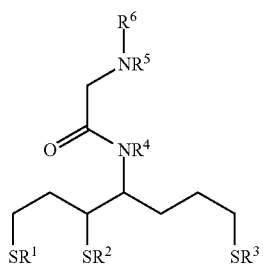
IV

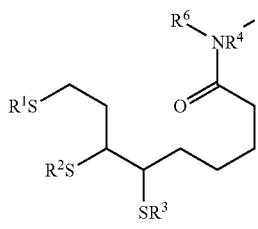
V

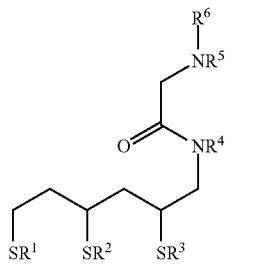
VI wherein $R^1$, $R^2$, and $R^3$, when taken alone, are independently H, halo, hydroxyl, (—(C=O)—$C_1$-$C_{22}$ or —(C=O)$CF_3$) alkanoyl, $C_1$-$C_{22}$ alkyl, $C_1$-$C_{22}$ heteroalkyl, ((CO)O$C_1$-$C_{22}$) alkylcarbonato, or —(CO)NH($C_1$-$C_{20}$) or —(CO)N($C_1$-$C_{20}$)$_2$) alkylcarbamoyl;

$R^4$, and $R^5$, when taken alone, are independently H, $C_1$-$C_{20}$ alkyl, or $C_6$-$C_{18}$ aryl; and $R^6$ is H or a polyethylene glycol moiety; and maintaining the mixture under conditions that cause the plurality of nanocrystals to migrate into an aqueous phase.

11. The method for producing a population of nanoparticles, as recited in claim 10, wherein the hydrophilic ligands are tridentate thiols.

12. The method for producing a population of nanoparticles, as recited in claim 10, wherein the hydrophilic ligands are dipeptides.

13. The method for producing a population of nanoparticles, as recited in claim 10, wherein the population of nanoparticles further comprises donor moieties or acceptor moieties, wherein the nanoparticles undergo FRET with the donor moieties or acceptor moieties.

14. The method for producing a population of nanoparticles, as recited in claim 13, wherein the population of nanoparticles has a FRET efficiency of greater than 20%.

15. A method for producing a population of FRET capable nanoparticles, comprising:

providing a mixture comprising a plurality of nanocrystal cores and at least one coordinating solvent;

adding a first intermediate shell precursor alternately with a second intermediate shell precursor in layer additions to form an intermediate shell layer comprising more than one monolayer on each of the plurality of nanocrystal cores;

adding a first external shell precursor alternately with a second external shell precursor in layer additions to form an external shell layer on each of the plurality of nanocrystal cores, wherein the external shell layer is disposed on top of the intermediate shell layer and is comprised of more than one monolayer;

adding an aqueous solution comprising hydrophilic ligands, wherein each hydrophilic ligand comprises a hydrophilic functional group that imparts aqueous dispersibility to the nanocrystal, wherein the hydrophilic ligands are selected from dipeptides, tridentate thiol ligands, and functionalized phosphonate or phosphinate ligands, wherein the tridentate thiol ligands are selected from the group consisting of compounds of Formula I, II, III, IV, V, or VI:

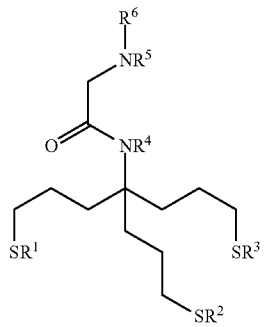
I

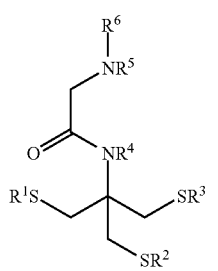
II

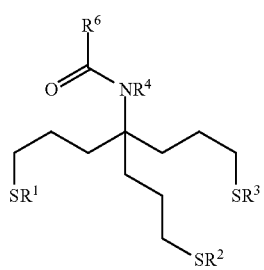
III

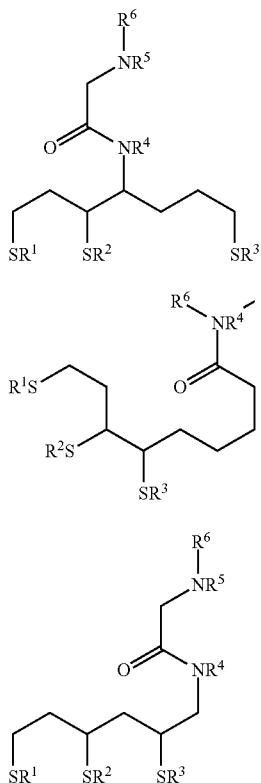
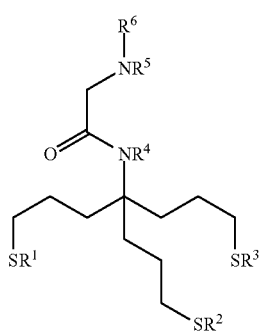
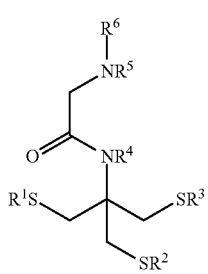
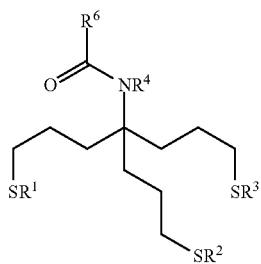
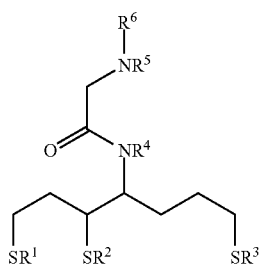
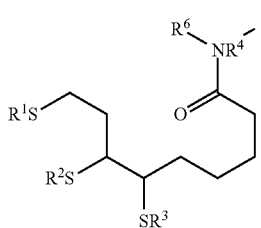

wherein $R^1$, $R^2$, and $R^3$, when taken alone, are independently H, halo, hydroxyl, (—(C=O)—$C_1$-$C_{22}$ or —(C=O)$CF_3$) alkanoyl, $C_1$-$C_{22}$ alkyl, $C_1$-$C_{22}$ heteroalkyl, ((CO)O$C_1$-$C_{22}$) alkylcarbonato, or (—(CO)NH($C_1$-$C_{20}$) or —(CO)N($C_1$-$C_{20}$)$_2$) alkylcarbamoyl;

$R^4$, and $R^5$, when taken alone, are independently H, $C_1$-$C_{20}$ alkyl, or $C_6$-$C_{18}$ aryl; and $R^6$ is H or a polyethylene glycol moiety; and maintaining the mixture under conditions that cause the plurality of nanocrystals to migrate into an aqueous phase, wherein, the population of FRET capable nanoparticles has a FRET efficiency of greater than about 20%.

16. The method for producing a population of FRET capable nanoparticles, as recited in claim 15, wherein the hydrophilic ligands are tridentate thiols.

17. The method for producing a population of FRET capable nanoparticles, as recited in claim 15, wherein the hydrophilic ligands are dipeptides.

18. The method for producing a population of FRET capable nanoparticles, as recited in claim 15, wherein the population of FRET capable nanoparticles has an on-time fraction of greater than 0.80.

19. A method for producing a population of nanoparticles, comprising:

providing a mixture comprising a plurality of nanocrystal cores, hydrophilic ligands and at least one coordinating solvent, wherein each hydrophilic ligand comprises a hydrophilic functional group that imparts aqueous dispersibility to the nanocrystal, wherein the hydrophilic ligands are selected from dipeptides, tridentate thiol ligands, and functionalized phosphonate or phosphinate ligands, wherein the tridentate thiol ligands are selected from the group consisting of compounds of Formula I, II, III, IV, V, or VI:

-continued

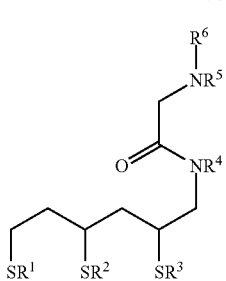

VI wherein $R^1$, $R^2$, and $R^3$, when taken alone, are independently H, halo, hydroxyl, (—(C=O)—$C_1$-$C_{22}$ or —(C=O)$CF_3$) alkanoyl, $C_1$-$C_{22}$ alkyl, $C_1$-$C_{22}$ heteroalkyl, ((CO)O$C_1$-$C_{22}$) alkylcarbonato, or (—(CO)NH($C_1$-$C_{20}$) or —(CO)N($C_1$-$C_{20}$)$_2$) alkylcarbamoyl;

$R^4$, and $R^5$, when taken alone, are independently H, $C_1$-$C_{20}$ alkyl, or $C_6$-$C_{18}$ aryl; and $R^6$ is H or a polyethylene glycol moiety;

adding a first intermediate shell precursor alternately with a second intermediate shell precursor in layer additions to form an intermediate shell layer comprising more than one monolayer on each of the plurality of nanocrystal cores; and adding a first external shell precursor alternately with a second external shell precursor in layer additions to form an external shell layer on each of the plurality of nanocrystal cores.

20. The method for producing a population of nanoparticles, as recited in claim 19, wherein the hydrophilic ligands are functionalized phosphonates.

21. The method for producing a population of nanoparticles, as recited in claim 19, wherein the hydrophilic ligands are functionalized phosphinates.

22. The method for producing a population of nanoparticles, as recited in claim 19, wherein the population of nanoparticles further comprises donor moieties or acceptor moieties, wherein the nanoparticles undergo FRET with the donor moieties or acceptor moieties.

23. The method for producing a population of nanoparticles, as recited in claim 22, wherein the population of nanoparticles has a FRET efficiency of greater than 20%.

24. The method for producing a population of nanoparticles, as recited in claim 19, wherein greater than 75% of the population of nanoparticles have diameters of less than about 15 nm.

25. The population of claim 1, wherein the polyethylene glycol moiety is a compound of Formula VII:

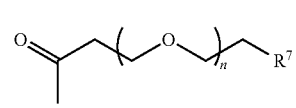

VII wherein $R^7$ is $NH_2$, $N_3$, NHBoc, NHFmoc, NHCbz, COOH, COOt-Bu, COOMe, iodoaryl, hydroxyl, alkyne, boronic acid, allylic alcohol carbonate, NHBiotin, (CO)NHNHBoc, (CO)NHNHFmoc, or OMe, wherein n is an integer from 1 to 100.

26. The population of claim 1, wherein the population of nanoparticles has an $\alpha_{on}$ value of less than about 1.4.

27. The method of claim 10, wherein the population of nanoparticles has an $\alpha_{on}$ value of less than about 1.4.

28. The method of claim 19, wherein the population of nanoparticles has an $\alpha_{on}$ value of less than about 1.4.

* * * * *